(12) United States Patent
Okada et al.

(10) Patent No.: US 6,461,747 B1
(45) Date of Patent: Oct. 8, 2002

(54) HETEROCYCLIC COMPOUNDS, MATERIALS FOR LIGHT EMITTING DEVICES AND LIGHT EMITTING DEVICES USING THE SAME

(75) Inventors: Hisashi Okada; Toshihiro Ise, both of Kanagawa (JP)

(73) Assignee: Fuji Photo Co., Ltd., Kanagawa (JP)

( * ) Notice: Subject to any disclaimer, the term of this patent is extended or adjusted under 35 U.S.C. 154(b) by 132 days.

(21) Appl. No.: 09/621,740

(22) Filed: Jul. 21, 2000

(30) Foreign Application Priority Data

Jul. 22, 1999 (JP) ............................................ 11-207957
Mar. 22, 2000 (JP) ........................................ 2000-080734

(51) Int. Cl.$^7$ ........................ H05B 33/14; C07D 471/00
(52) U.S. Cl. ........................ 428/690; 428/704; 428/917; 313/504; 313/506; 252/301.16; 252/301.26; 252/301.27; 252/301.28; 252/301.31; 546/113; 546/114; 546/115; 546/118; 548/152; 548/153; 548/217; 548/218; 548/219; 548/302.7; 548/303.1; 548/453; 548/121
(58) Field of Search ................................. 428/690, 704, 428/917; 313/504, 506; 252/301.16, 301.26, 301.31, 301.27, 301.28; 546/113, 114, 115, 118; 548/152, 153, 217, 218, 219, 302.7, 303.1, 453, 121

(56) References Cited

U.S. PATENT DOCUMENTS 5,085,946 A * 2/1992 Saito et al. .................. 428/690

FOREIGN PATENT DOCUMENTS

DE           WO-9804007      * 1/1998

* cited by examiner

*Primary Examiner*—Cynthia H. Kelly
*Assistant Examiner*—Ling Xu
(74) *Attorney, Agent, or Firm*—Sughrue Mion, PLLC

(57) ABSTRACT

Disclosed is a material for a light emitting device excellent in color purity, good in light emitting characteristics and excellent in stability, which consists of a compound represented by the following general formula (I):

$$L\text{-}(A)_m \quad (I)$$

wherein A represents a heterocyclic group in which two or more aromatic heterocycles are condensed; m represents an integer of 2 or more, and the heterocyclic groups represented by A may be the same or different; and L represents a connecting group.

11 Claims, No Drawings

US 6,461,747 B1

HETEROCYCLIC COMPOUNDS, MATERIALS FOR LIGHT EMITTING DEVICES AND LIGHT EMITTING DEVICES USING THE SAME

FIELD OF THE INVENTION

The present invention relates to novel heterocyclic compounds, and more particularly to materials for light emitting devices that can convert electric energy to light to emit the light. The invention further relates to light emitting devices which can be suitably used in the fields of display elements, displays, back lights, electrophotography, illuminating light sources, recording light sources, reading light sources, indicators, signboards and interior decorations.

BACKGROUND OF THE INVENTION

At present, the research and development of various display elements have been actively made. In particular, organic electroluminescence (EL) devices have attracted attention as promising display devices, because luminescence of high luminance can be obtained at low voltage. For example, a light emitting device in which an organic thin film is formed by vapor deposition of an organic compound (*Applied Physics Letters*, 51, 913 (1987)) has been known. The light emitting device described in this literature is substantially improved in light emitting characteristics compared with conventional monolayer elements, by using tris(8-hydroxyquinolinato)aluminum complex (Alq) as an electron transporting material and laminating a hole transporting material (amine compound) therewith.

As means for further improving the light emitting efficiency of the laminated light emitting devices, methods of doping the elements with fluorescent dyes have been known. For example, elements doped with coumarin dyes, described in *Journal of Applied Physics*, 65, 3610 (1989), are substantially improved in light emitting efficiency compared with elements not doped therewith. In this case, it is possible to take out light having a desired wavelength by changing the kind of fluorescent compound. However, when Alq is used as the electron transporting material, an increase in driving voltage for obtaining high luminance results in observation of green luminescence of Alq in addition to luminescence of the fluorescent compound used for doping. Accordingly, blue luminescence suffers from the problem of a reduction in color purity, so that the development of host materials which do not reduce the color purity has been desired. For improving this disadvantage, specified indole derivatives are disclosed in JP-A-10-92578 (the term "JP-A" as used herein means an "unexamined published Japanese patent application") and U.S. Pat. No. 5,766,779. However, the compounds described therein have the problem that an increase in driving voltage is required for luminescence of high luminance. Accordingly, the development of compounds in which luminescence of high luminance is possible at low voltage has been desired.

As methods for increasing the light emitting efficiency, methods are reported in which hole blocking materials such as 3-(4-biphenylyl)-4-phenyl-5-(4-tert-butylphenyl)-1,2,4-triazole (TAZ) and bathocuproin (BCP) are used. However, the use of these known materials has raised a serious problem with regard to durability, particularly deterioration of the elements with time in storing at high temperatures in continuous luminescence.

The conventional elements good in color purity and high in light emitting efficiency are ones in which charge transporting materials are doped with fluorescent dyes in slight amounts, and have the problems that it is difficult to give the reproducibility of element characteristics from the production point of view, and that the long-term use thereof causes a reduction in luminance and changes in color because of low durability of the dyes. As means for solving the problems, the development of materials having both the charge transporting function and the luminescent function has been desired. However, the materials that have hitherto been developed have the problem that the use of fluorescent dyes at high concentrations results in difficulty in emitting light of high luminance by concentration quenching or association.

On the other hand, organic light emitting devices realizing luminescence of high luminance are elements in which organic materials are applied by vacuum deposition. The fabrication of the elements by coating is preferred from the viewpoints of simplification of manufacturing processes, processability and enlargement of area. However, the elements fabricated by the conventional coating system are inferior in luminance and light emitting efficiency to the element fabricated by vapor deposition. It has been therefore a great problem to make it possible to emit light of high luminance at high efficiency.

SUMMARY OF THE INVENTION

It is therefore a primary object of the present invention to provide materials for light emitting devices good in light emitting characteristics and excellent in stability in repeated use thereof, and the light emitting devices. A secondary object of the present invention is to provide light emitting devices excellent in color purity, and materials for the light emitting devices making it possible. A third object of the present invention is to provide novel heterocyclic compounds effective in various electronic devices.

These objects have been attained by the following means:

(1) A material for a light emitting device consisting of a compound represented by the following general formula (I):

(I)

wherein A represents a heterocyclic group in which two or more aromatic heterocycles are condensed; m represents an integer of 2 or more, and the heterocyclic groups represented by A may be the same or different; and L represents a connecting group;

(2) A material for a light emitting device consisting of a compound represented by the following general formula (II):

(II)

wherein B represents a heterocyclic group in which two or more 5-and/or 6-membered aromatic heterocycles are condensed; m represents an integer of 2 or more, and the heterocyclic groups represented by B may be the same or different; and L represents a connecting group;

(3) A material for a light emitting device consisting of a compound represented by the following general formula (III):

(III)

wherein X represents O, S, Se, Te or N—R; R represents a hydrogen atom, an aliphatic hydrocarbon group, an aryl group or a heterocyclic group; $Q_3$ represents an atomic group necessary to form an aromatic heterocycle; m represents an integer of 2 or more; and L represents a connecting group;

(4) A material for a light emitting device consisting of a compound represented by the following general formula (IV):

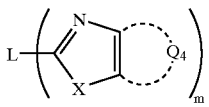

(IV)

wherein X represents O, S, Se, Te or N—R; R represents a hydrogen atom, an aliphatic hydrocarbon group, an aryl group or a heterocyclic group; $Q_4$ represents an atomic group necessary to form a nitrogen-containing aromatic heterocycle; m represents an integer of 2 or more; and L represents a connecting group;

(5) A material for a light emitting device consisting of a compound represented by the following general formula (V):

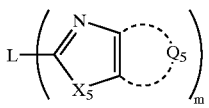

(V)

wherein $X_5$ represents O, S or N—R; R represents a hydrogen atom, an aliphatic hydrocarbon group, an aryl group or a heterocyclic group; $Q_5$ represents an atomic group necessary to form a 6-membered nitrogen-containing aromatic heterocycle; m represents an integer of 2 or more; and L represents a connecting group;

(6) A material for a light emitting device consisting of a compound represented by the following general formula (VI):

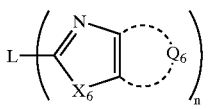

(VI)

wherein $X_6$ represents O, S or N—R; R represents a hydrogen atom, an aliphatic hydrocarbon group, an aryl group or a heterocyclic group; $Q_6$ represents an atomic group necessary to form a 6-membered nitrogen-containing aromatic heterocycle; n represents an integer of 2 to 8; and L represents a connecting group;

(7) A material for a light emitting device consisting of a compound represented by the following general formula (VII):

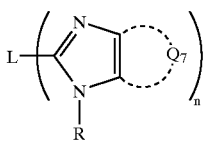

(VII)

wherein R represents a hydrogen atom, an aliphatic hydrocarbon group, an aryl group or a heterocyclic group; $Q_7$ represents an atomic group necessary to form a 6-membered nitrogen-containing aromatic heterocycle; n represents an integer of 2 to 8; and L represents a connecting group;

(8) A material for a light emitting device consisting of a compound represented by the following general formula (VIII):

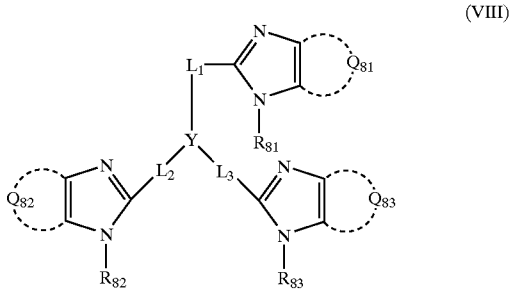

(VIII)

wherein $Q_{81}$, $Q_{82}$ and $Q_{83}$ each represents an atomic group necessary to form a 6-membered nitrogen-containing aromatic heterocycle; $R_{81}$, $R_{82}$ and $R_{83}$ each represents a hydrogen atom, an aliphatic hydrocarbon group, an aryl group or a heterocyclic group; $L_1$, $L_2$, and $L_3$ each represents a connecting group; and Y represents a nitrogen atom or a 1,3,5-benzenetriyl group;

(9) A compound represented by the following general formula (IX):

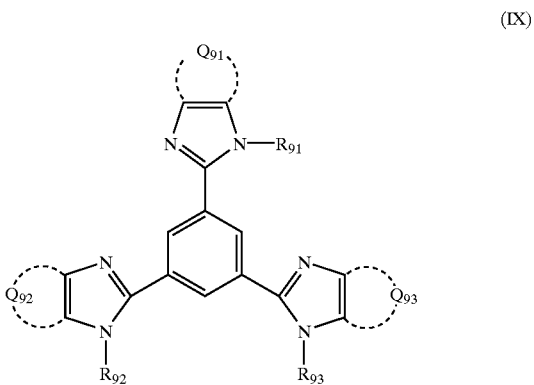

(IX)

wherein $Q_{91}$, $Q_{92}$ and $Q_{93}$ each represents an atomic group necessary to form a 6-membered nitrogen-containing aromatic heterocycle; and $R_{91}$, $R_{92}$ and $R_{93}$ each represents a hydrogen atom, an aliphatic hydrocarbon group, an aryl group or a heterocyclic group;

(10) A compound represented by the following general formula (X):

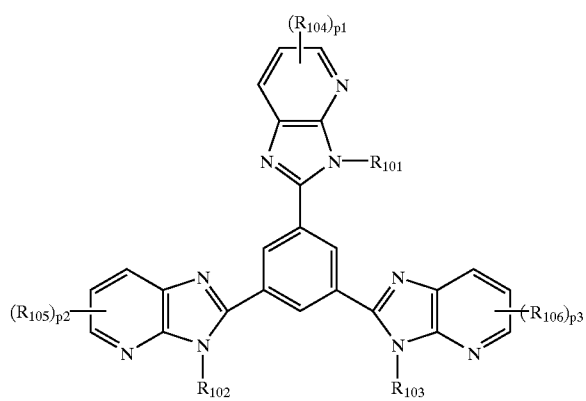

(X)

wherein $R_{101}$, $R_{102}$ and $R_{103}$ each represents a hydrogen atom, an aliphatic hydrocarbon group, an aryl group or a heterocyclic group; $R_{104}$, $R_{105}$ and $R_{106}$ each represents a substituent; and $p_1$, $p_2$ and $p_3$ each represents an integer of 0 to 3;

(11) A material for a light emitting device consisting of a compound represented by the following general formula (XI):

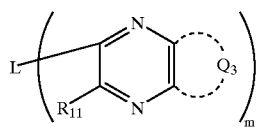

wherein $Q_3$ represents an atomic group necessary to form an aromatic heterocycle; $R_{11}$ represents a hydrogen atom or a substituent; m represents an integer of 2 or more; and L represents a connecting group;

(12) A light emitting device comprising a light emitting layer or a plurality of organic compound films containing a light emitting layer formed between a pair of electrodes, wherein at least one layer is a layer containing at least one of the compounds represented by general formula (I) to (XI) described in (1) to (11);

(13) A light emitting device comprising a light emitting layer or a plurality of organic compound films containing a light emitting layer formed between a pair of electrodes, wherein at least one layer is a layer in which at least one of the compounds represented by general formula (I) to (XI) described in (1) to (11) is dispersed in a polymer;

(14) A light emitting device comprising a light emitting layer or a plurality of organic compound films containing a light emitting layer formed between a pair of electrodes, wherein at least one layer between the light emitting layer and a cathode is a layer containing at least one of the compounds represented by general formula (I) to (XI) described in (1) to (11);

(15) A light emitting device comprising a light emitting layer or a plurality of organic compound films containing a light emitting layer formed between a pair of electrodes, wherein at least one layer between a blue light emitting layer and a cathode is a layer containing at least one of the compounds represented by general formula (I) to (XI) described in (1) to (11); and

(16) A light emitting device comprising a light emitting layer or a plurality of organic compound films containing a light emitting layer formed between a pair of electrodes, wherein a layer containing at least one of the compounds represented by general formula (I) to (XI) described in (1) to (11) contains a blue light emitting material.

DETAILED DESCRIPTION OF THE INVENTION

The invention will be described in detail below.

First, the compounds represented by general formula (I) will be described.

A represents a heterocyclic group in which two or more aromatic heterocycles are condensed. The heterocyclic groups represented by A may be the same or different.

The heterocyclic group represented by A is preferably a condensation product of 5- or 6-membered aromatic heterocycles, more preferably 2 to 6 aromatic heterocycles, still more preferably 2 or 3 aromatic heterocycles, and particularly preferably 2 aromatic heterocycles. In this case, the heteroatom is preferably an N, O, S, Se or Te atom, more preferably an N, O or S atom, and still more preferably an N atom.

The specific examples of the aromatic heterocycles constituting the heterocyclic groups represented by A include, for example, furan, thiophene, pyran, pyrrole, imidazole, pyrazole, pyridine, pyrazine, pyrimidine, pyridazine, thiazole, oxazole, isothiazole, isoxazole, thiadiazole, oxadiazole, triazole, selenazole and tellurazole, preferably imidazole, pyrazole, pyridine, pyrazine, pyrimidine, pyridazine, thiazole and oxazole, and more preferably imidazole, thiazole, oxazole, pyridine, pyrazine, pyrimidine and pyridazine.

Specific examples of the condensed rings represented by A include, for example, indolizine, purine, pteridine, carboline, pyrroloimidazole, pyrrolotriazole, pyrazoloimidazole, pyrazolotriazole, pyrazolopyrimidine, pyrazolotriazine, triazolopyridine, tetraazaindene, imidazoimidazole, imidazopyridine, imidazopyrazine, imidazopyrimidine, imidazopyridazine, oxazolopyridine, oxazolopyrazine, oxazolopyrimidine, oxazolopyridazine, thiazolopyridine, thiazolopyrazine, thiazolopyrimidine, thiazolopyridazine, pyridinopyrazine, pyradinopyrazine, pyradinopyridazine, naphthyridine and imidazotriazine, preferably imidazopyridine, imidazopyrazine, imidazopyrimidine, imidazopyridazine, oxazolopyridine, oxazolo-pyrazine, oxazolopyrimidine, oxazolopyridazine, thiazolopyridine, thiazolopyrazine, thiazolopyrimidine, thiazolopyridazine, pyridinopyrazine and pyradinopyrazine, more preferably imidazopyridine, oxazolopyridine, thiazolopyridine, pyridinopyrazine and pyradinopyrazine, and particularly preferably imidazopyridine.

The heterocyclic group represented by A may be further condensed with another ring, and may have a substituent. The substituents of the heterocyclic groups represented by A include, for example, alkyl groups (each having preferably 1 to 30 carbon atoms, more preferably 1 to 20 carbon atoms, and particularly preferably 1 to 10 carbon atoms, such as methyl, ethyl, iso-propyl, tert-butyl, n-octyl, n-decyl, n-hexadecyl, cyclopropyl, cyclopentyl and cyclohexyl), alkenyl groups (each having preferably 2 to 30 carbon atoms, more preferably 2 to 20 carbon atoms, and particularly preferably 2 to 10 carbon atoms, such as vinyl, allyl, 2-butenyl and 3-pentenyl), alkynyl groups (each having preferably 2 to 30 carbon atoms, more preferably 2 to 20 carbon atoms, and particularly preferably 2 to 10 carbon atoms, such as propargyl and 3-pentynyl), aryl groups (each having preferably 6 to 30 carbon atoms, more preferably 6 to 20 carbon atoms, and particularly preferably 6 to 12 carbon atoms, such as phenyl, p-methylphenyl and naphthyl), amino groups (each having preferably 0 to 30 carbon atoms, more preferably 0 to 20 carbon atoms, and particularly preferably 0 to 10 carbon atoms, such as amino, methylamino, dimethylamino, diethylamino, dibenzylamino, diphenylamino and ditolylamino), alkoxyl groups (each having preferably 1 to 30 carbon atoms, more preferably 1 to 20 carbon atoms, and particularly preferably 1 to 10 carbon atoms, such as methoxy, ethoxy, butoxy and 2-ethylhexyloxy), aryloxy groups (each having preferably 6 to 30 carbon atoms, more preferably 6 to 20 carbon atoms, and particularly preferably 6 to 12 carbon atoms, such as phenyloxy, 1-naphthyloxy and 2-naphthyloxy), acyl groups (each having preferably 1 to 30 carbon atoms, more preferably 1 to 20 carbon atoms, and particularly preferably 2 to 12 carbon atoms, such as acetyl, benzoyl, formyl and pivaloyl), alkoxycarbonyl groups (each having preferably 2 to 30 carbon atoms, more preferably 2 to 20 carbon atoms, and particularly preferably 2 to 12 carbon atoms, such as methoxycarbonyl and ethoxycarbonyl), aryloxycarbonyl groups (each having preferably 7 to 30 carbon atoms, more preferably 7 to 20 carbon atoms, and particularly preferably 7 to 12 carbon atoms, such as phenyloxycarbonyl), acyloxy groups (each having preferably 2 to 30 carbon atoms, more preferably 2 to 20 carbon atoms, and particularly preferably 2 to 10 carbon atoms, such as acetoxy and benzoyloxy), acylamino groups (each having preferably 2 to 30 carbon atoms, more preferably 2 to 20 carbon atoms, and particularly preferably 2 to 10 carbon atoms, such as acetylamio and benzoylamino), alkoxycarbonylamino groups (each having preferably 2 to 30 carbon atoms, more preferably 2 to 20 carbon atoms, and particularly preferably 2 to 12 carbon atoms, such as methoxycarbonylamino), aryloxycarbonylamino groups (each having preferably 7 to 30 carbon atoms, more preferably 7 to 20 carbon atoms, and particularly preferably 7 to 12 carbon atoms, such as phenyloxycarbonylamino), sulfonylamino groups (each having preferably 1 to 30 carbon atoms, more preferably 1 to 20 carbon atoms, and particularly preferably 1 to 12 carbon atoms, such as methanesulfonylamino and benzenesulfonylamino), sulfamoyl groups (each having preferably 0 to 30 carbon atoms, more preferably 0 to 20 carbon atoms, and particularly preferably 0 to 12 carbon atoms, such as sulfamoyl, methylsulfamoyl, dimethylsulfamoyl and phenylsulfamoyl), carbamoyl groups (each having preferably 1 to 30 carbon atoms, more preferably 1 to 20 carbon atoms, and particularly preferably 1 to 12 carbon atoms, such as carbamoyl, methylcarbamoyl, diethylcarbamoyl and phenylcarbamoyl), alkylthio groups (each having preferably 1 to 30 carbon atoms, more preferably 1 to 20 carbon atoms, and particularly preferably 1 to 12 carbon atoms, such as methylthio and ethylthio), arylthio groups (each having preferably 6 to 30 carbon atoms, more preferably 6 to 20 carbon atoms, and particularly preferably 6 to 12 carbon atoms, such as phenylthio), sulfonyl groups (each having preferably 1 to 30 carbon atoms, more preferably 1 to 20 carbon atoms, and particularly preferably 1 to 12 carbon atoms, such as mesyl and tosyl), sulfinyl groups (each having preferably 1 to 30 carbon atoms, more preferably 1 to 20 carbon atoms, and particularly preferably 1 to 12 carbon atoms, such as methanesulfinyl and benzenesulfinyl), ureido groups (each having preferably 1 to 30 carbon atoms, more preferably 1 to 20 carbon atoms, and particularly preferably 1 to 12 carbon atoms, such as ureido, methylureido and phenylureido), phosphoric acid amide groups (each having preferably 1 to 30 carbon atoms, more preferably 1 to 20 carbon atoms, and particularly preferably 1 to 12 carbon atoms, such as diethylphosphoric acid amide and phenylphosphoric acid amide), hydroxyl, mercapto, halogen atoms (such as fluorine, chlorine, bromine and iodine), cyano, sulfo, carboxyl, nitro, hydroxamic acid groups, sulfino, hydrazino, imino, heterocyclic groups (each having preferably 1 to 30 carbon atoms, and more preferably 1 to 12 carbon atoms, having heteroatoms such as nitrogen, oxygen and sulfur, and specifically including imidazolyl, pyridyl, quinolyl, furyl, thienyl, piperidyl, morpholino, benzoxazolyl, benzimidazolyl and benzthiazolyl, carbazolyl and azepinyl), and silyl groups (each having preferably 3 to 40 carbon atoms, more preferably 3 to 30 carbon atoms, and particularly preferably 3 to 24 carbon atoms, such as trimethylsilyl and triphenylsilyl). These substituents may be further substituted. When there are two or more substituents, they may be the same or different. Further, they may be combined to form a ring if possible.

The substituents of the heterocyclic groups represented by A are preferably alkyl, alkenyl, alkynyl, aryl, amino, alkoxyl, aryloxy, acyl, alkoxycarbonyl, aryloxycarbonyl, acyloxy, acylamino, alkoxycarbonylamino, aryloxycarbonylamino, sulfonylamino, sulfamoyl, carbamoyl, alkylthio, arylthio, sulfonyl, cyano and heterocyclic groups and halogen atoms, more preferably alkyl, alkenyl, aryl, alkoxyl, aryloxy, cyano and heterocyclic groups and halogen atoms, still more preferably alkyl, aryl, alkoxyl, aryloxy and aromatic heterocyclic groups, and particularly preferably alkyl, aryl, alkoxyl and aromatic heterocyclic groups.

m represents an integer of 2 or more, preferably 2 to 8, more preferably 2 to 6, still more preferably 2 to 4, particularly preferably 2 or 3, and most preferably 3.

L represents a connecting group. The connecting group represented by L is preferably a single bond or a connecting group formed by C, N, O, S, Si or Ge, more preferably a single bond or a group comprising alkylene, alkenylene, alkynylene, arylene, a divalent heterocycle (preferably an aromatic heterocycle, and more preferably an aromatic heterocycle formed by an azole, thiophene or furan ring) or a combination thereof with N, and still more preferably a group comprising arylene, a divalent aromatic heterocycle or a combination thereof with N.

Specific examples of the connecting groups represented by L include, for example, the following groups, as well as a single bond.

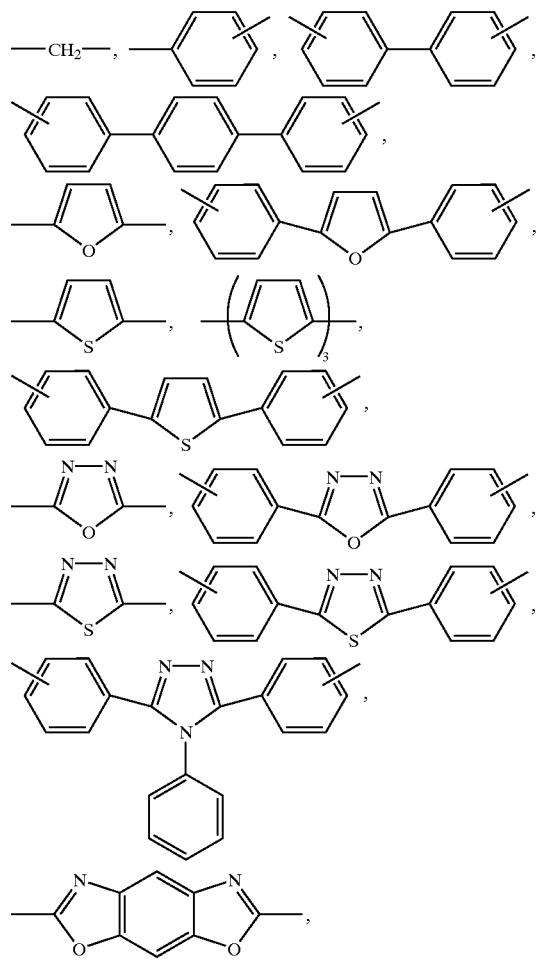

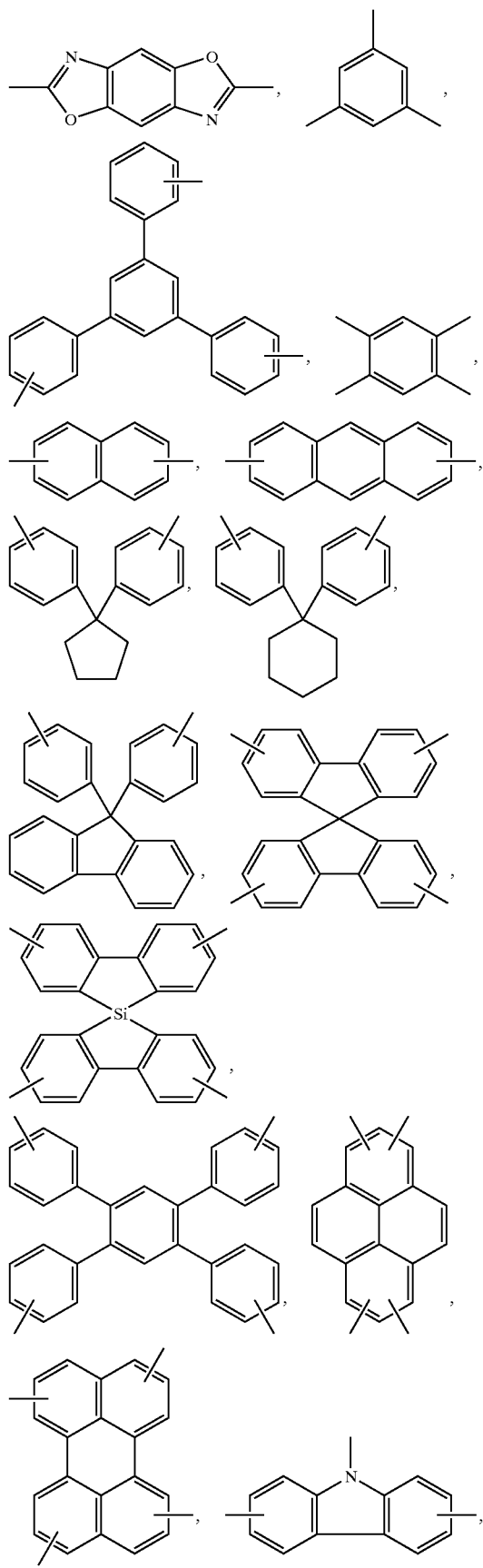
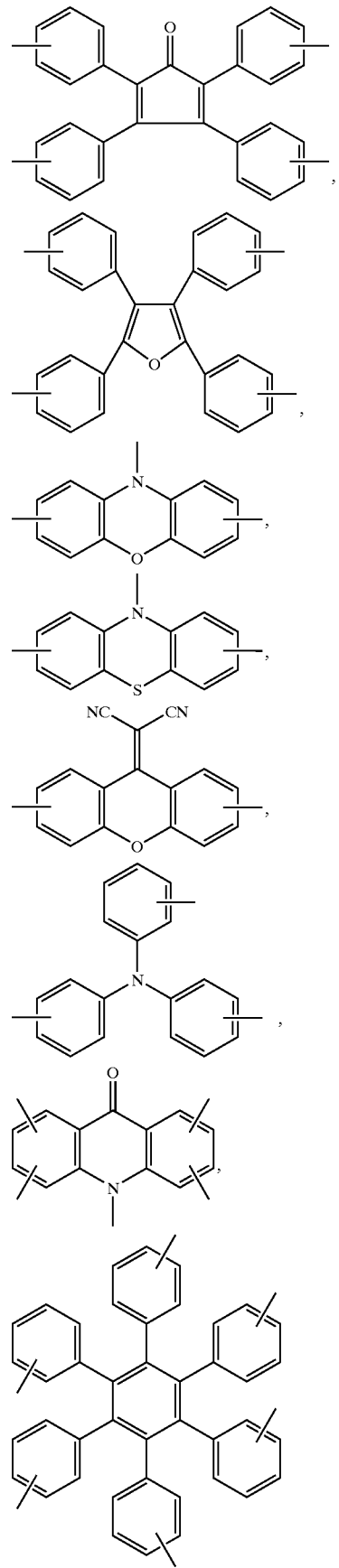

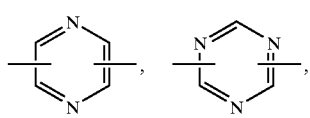
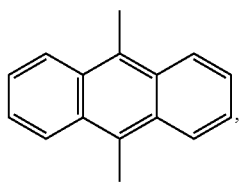
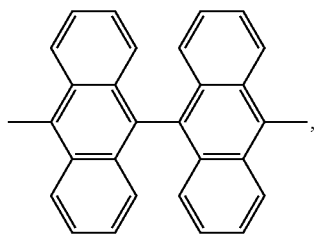
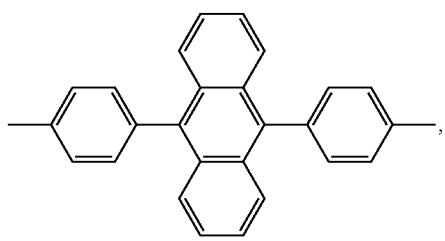
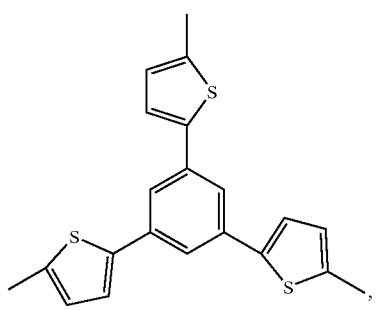
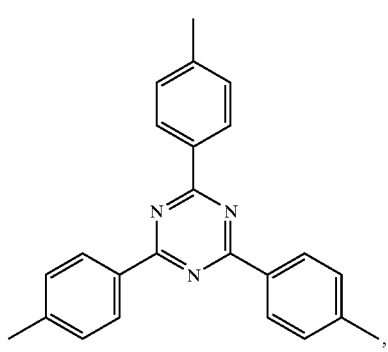
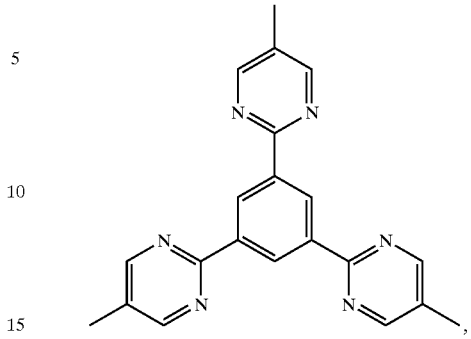
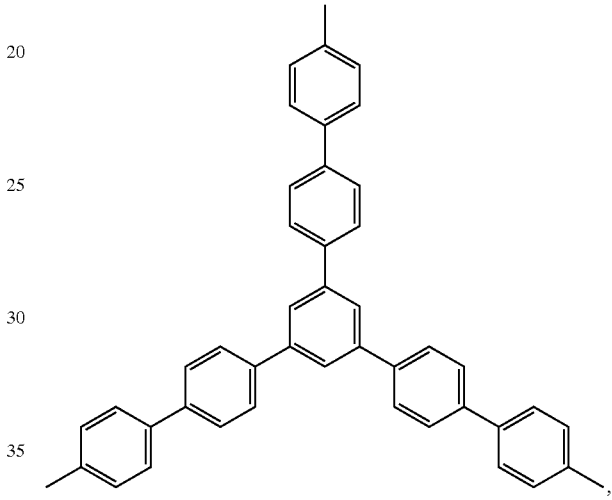
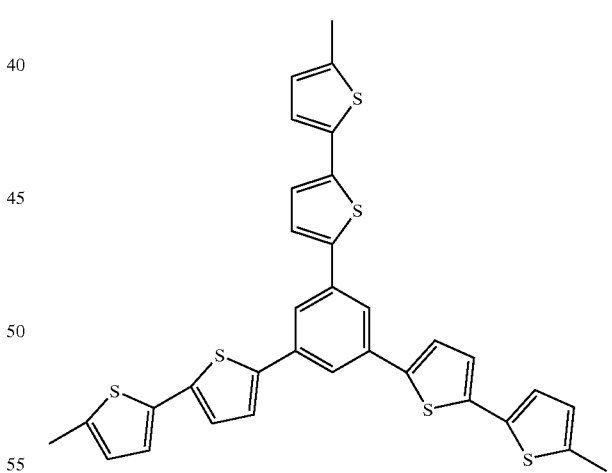
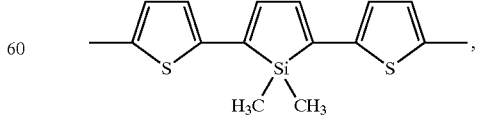

The connecting group represented by L may have a substituent. For example, the substituents of the heterocyclic groups represented by A can be applied as the substituents. The substituents of L are preferably alkyl, alkenyl, alkynyl, aryl, alkoxyl, aryloxy, acyl, cyano, heterocyclic and silyl groups and halogen atoms, more preferably alkyl, alkenyl, alkynyl, aryl, alkoxyl, aryloxy, cyano and aromatic heterocyclic groups and halogen atoms, and still more preferably alkyl, aryl and aromatic heterocyclic groups.

Of the compounds represented by general formula (I), preferred are compounds represented by the following general formula (II):

$$L-(B)_m \quad (II)$$

wherein m and L each has the same meaning as given for general formula (I), and each preferred range is also the same as given therefor; and B represents a heterocyclic group in which two or more 5- and/or 6-membered aromatic heterocycles are condensed, and the heterocyclic groups represented by B may be the same or different.

The heterocyclic group represented by B is preferably a condensation product of 2 to 6, 5- or 6-membered aromatic heterocycles, more preferably 2 or 3 aromatic heterocycles, and particularly preferably 2 aromatic heterocycles. In this case, the heteroatom is preferably an N, O, S, Se or Te atom, more preferably an N, O or S atom, and still more preferably an N atom.

Specific examples of the aromatic heterocycles constituting the heterocyclic groups represented by B include, for example, furan, thiophene, pyran, pyrrole, imidazole, pyrazole, pyridine, pyrazine, pyrimidine, pyridazine, thiazole, oxazole, isothiazole, isoxazole, thiadiazole, oxadiazole, triazole, selenazole and tellurazole, preferably imidazole, pyrazole, pyridine, pyrazine, pyrimidine, pyridazine, thiazole and oxazole, and more preferably imidazole, thiazole, oxazole, pyridine, pyrazine, pyrimidine and pyridazine.

Specific examples of the condensed rings represented by B include, for example, indolizine, purine, pteridine, carboline, pyrroloimidazole, pyrrolotriazole, pyrazoloimidazole, pyrazolotriazole, pyrazolopyrimidine, pyrazolotriazine, triazolopyridine, tetraazaindene, imidazoimidazole, imidazopyridine, imidazopyrazine, imidazopyrimidine, imidazopyridazine, oxazolopyridine, oxazolopyrazine, oxazolopyrimidine, oxazolopyridazine, thiazolopyridine, thiazolopyrazine, thiazolopyrimidine, thiazolopyridazine, pyridinopyrazine, pyrazinopyrazine, pyrazinopyridazine, naphthilidine and imidazotriazine, preferably imidazopyridine, imidazopyrazine, imidazopyrimidine, imidazopyridazine, oxazolopyridine, oxazolo-pyrazine, oxazolopyrimidine, oxazolopyridazine, thiazolopyridine, thiazolopyrazine, thiazolopyrimidine, thiazolopyridazine, pyridinopyrazine and pyrazinopyrazine, more preferably imidazopyridine, oxazolopyridine, thiazolopyridine, pyridinopyrazine and pyrazinopyrazine, and particularly preferably imidazopyridine.

The heterocyclic group represented by B may have a substituent. As the substituents, the substituents of the heterocyclic groups represented by A in general formula (I) can be applied, and preferred substituents are also the same as given therefor.

Of the compounds represented by general formula (I), more preferred are compounds represented by the following general formula

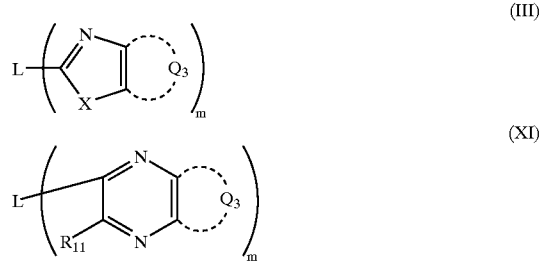

The compounds represented by general formula (III) will be explained.

In formula (III), m and L each has the same meaning as given for general formula (I), and each preferred range is also the same as given therefor; X represents O, S, Se, Te or N—R; R represents a hydrogen atom, an aliphatic hydrocarbon group, an aryl group or a heterocyclic group; and $Q_3$ represents an atomic group necessary to form an aromatic heterocycle.

The aliphatic hydrocarbon groups represented by R are preferably alkyl groups (each having preferably 1 to 20 carbon atoms, more preferably 1 to 12 carbon atoms, and particularly preferably 1 to 8 carbon atoms, such as methyl, ethyl, iso-propyl, tert-butyl, n-octyl, n-decyl, n-hexadecyl, cyclopropyl, cyclopentyl and cyclohexyl), alkenyl groups (each having preferably 2 to 20 carbon atoms, more preferably 2 to 12 carbon atoms, and particularly preferably 2 to 8 carbon atoms, such as vinyl, allyl, 2-butenyl and 3-pentenyl), alkynyl groups (each having preferably 2 to 20 carbon atoms, more preferably 2 to 12 carbon atoms, and particularly preferably 2 to 8 carbon atoms, such as propargyl and 3-pentynyl). More preferred are alkyl groups and alkenyl groups.

The aryl groups represented by R each has preferably 6 to 30 carbon atoms, more preferably 6 to 20 carbon atoms, and particularly preferably 6 to 12 carbon atoms, and examples thereof include phenyl, 2-methylphenyl, 3-methylphenyl, 4-methylphenyl, 4-methoxyphenyl, 3-trifluoromethylphenyl, pentafluorophenyl, 2-biphenyl, 3-biphenyl, 4-biphenyl, 1-naphthyl, 2-naphthyl and 1-pyrenyl.

The heterocyclic groups represented by R are monocyclic or condensed ring type heterocyclic groups (each having preferably 1 to 20 carbon atoms, more preferably 1 to 12 carbon atoms, and still more preferably 2 to 10 carbon atoms), and preferably aromatic heterocyclic groups each containing at least one of nitrogen, oxygen, sulfur and selenium atoms. Specific examples of the heterocyclic groups represented by R include pyrrolidine, piperidine, pyrrole, furan, thiophene, imidazoline, imidazole, benzimidazole, naphthimidazole, thiazolidine, thiazole, benzthiazole, naphthothiazole, isothiazole, oxazoline, oxazole, benzoxazole, naphthoxazole, isoxazole, selenazole, benzoselenazole, naphthoselenazole, pyridine, quinoline, isoquinoline, indole, indolenine, pyrazole, pyrazine, pyrimidine, pyridazine, triazine, indazole, purine, phthalazine, naphthyridine, quinoxaline, quinazoline, cinnoline, pteridine, phenanthridine, phenanthroline and tetraazaindene. Preferred are furan, thiophene, pyridine, quinoline, pyrazine, pyrimidine, pyridazine, triazine, phthalazine, naphthyridine, quinoxaline and quinazoline, more preferred are furan, thiophene, pyridine and quinoline, and particularly preferred is quinoline.

The aliphatic hydrocarbon group, aryl group and heterocyclic group represented by R may each have a substituent.

As the substituents, the substituents of the heterocyclic groups represented by A in general formula (I) can be applied, and preferred substituents are also the same as given therefor.

R is preferably an alkyl group, an aryl group or an aromatic heterocyclic group, more preferably an aryl group or an aromatic heterocyclic group, and still more preferably an aryl group or an aromatic azole group.

X is preferably O, S or N—R, more preferably O or N—R, still more preferably N—R, and particularly preferably N—Ar (wherein Ar is an aryl group or an aromatic azole group, preferably an aryl group having 6 to 30 carbon atoms or an aromatic azole group having 2 to 30 carbon atoms, more preferably an aryl group having 6 to 20 carbon atoms or an aromatic azole group having 2 to 16 carbon atoms, and particularly preferably an aryl group having 6 to 12 carbon atoms or an aromatic azole group having 2 to 10 carbon atoms).

$Q_3$ represents an atomic group necessary to form an aromatic heterocycle. The aromatic heterocycle formed by $Q_3$ is preferably a 5- or 6-membered aromatic heterocycle, more preferably a 5- or 6-membered nitrogen-containing aromatic heterocycle, and still more preferably a 6-membered nitrogen-containing aromatic heterocycle.

Specific examples of the aromatic heterocycles formed by $Q_3$ include, for example, furan, thiophene, pyran, pyrrole, imidazole, pyrazole, pyridine, pyrazine, pyrimidine, pyridazine, thiazole, oxazole, isothiazole, isoxazole, thiadiazole, oxadiazole, triazole, selenazole and tellurazole, preferably pyridine, pyrazine, pyrimidine and pyridazine, more preferably pyridine and pyrazine, and still more preferably pyridine.

The aromatic heterocycle formed by $Q_3$ may form a condensed ring with another ring, and may have a substituent. As the substituents, the substituents of the heterocyclic groups represented by A in general formula (I) can be applied, and preferred substituents are also the same as given therefor.

Of the compounds represented by general formula (III), still more preferred are compounds represented by the following general formula (IV):

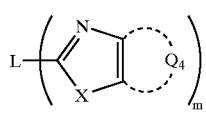

(IV)

wherein m and L each has the same meaning as given for general formula (I), and each preferred range is also the same as given therefor; X has the same meaning as given for general formula (III), and a preferred range is also the same as given therefor; and $Q_4$ represents an atomic group necessary to form a nitrogen-containing aromatic heterocycle.

The nitrogen-containing aromatic heterocycle formed by $Q_4$ is preferably a 5- or 6-membered nitrogen-containing aromatic heterocycle, and more preferably a 6-membered nitrogen-containing aromatic heterocycle.

Specific examples of the nitrogen-containing aromatic heterocycles formed by $Q_4$ include, for example, pyrrole, imidazole, pyrazole, pyridine, pyrazine, pyrimidine, pyridazine, thiazole, oxazole, isothiazole, isoxazole, thiadiazole, oxadiazole, triazole, selenazole and tellurazole, preferably pyridine, pyrazine, pyrimidine and pyridazine, more preferably pyridine and pyrazine, and still more preferably pyridine.

The aromatic heterocycle formed by $Q_4$ may form a condensed ring with another ring, and may have a substituent. As the substituents, the substituents of the heterocyclic groups represented by A in general formula (I) can be applied, and preferred substituents are also the same as given therefor.

Of the compounds represented by general formula (III), yet more preferred are compounds represented by the following general formula (V):

wherein m and L each has the same meaning as given for general formula (I), and each preferred range is also the same as given therefor; $X_5$ represents O, S or N—R; R has the same meaning as given for general formula (III), and a preferred range is also the same as given therefor; and $Q_5$ represents an atomic group necessary to form a 6-membered nitrogen-containing aromatic heterocycle.

Specific examples of the nitrogen-containing aromatic heterocycles formed by $Q_5$ include, for example, pyridine, pyrazine, pyrimidine, pyridazine and triazine, preferably pyridine, pyrazine, pyrimidine and pyridazine, more preferably pyridine and pyrazine, and still more preferably pyridine.

The nitrogen-containing aromatic heterocycles formed by $Q_5$ may form a condensed ring with another ring, and may have a substituent. As the substituents, the substituents of the heterocyclic groups represented by A in general formula (I) can be applied, and preferred substituents are also the same as given therefor.

Of the compounds represented by general formula (III), yet still more preferred are compounds represented by the following general formula (VI):

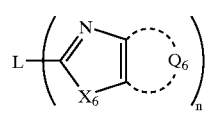

(VI)

wherein L has the same meaning as given for general formula (I), and a preferred range is also the same as given therefor; $X_6$ has the same meaning as given for $X_5$ in general formula (V), and a preferred range is also the same as given therefor; $Q_6$ has the same meaning as given for $Q_6$ in general formula (V), and a preferred range is also the same as given therefor; and n represents an integer of 2 to 8, preferably 2 to 6, more preferably 2 to 4, still more preferably 2 and 3, and particularly preferably 3.

Of the compounds represented by general formula (III), further preferred are compounds represented by the following general formula (VII):

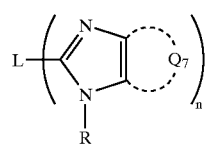

(VII)

wherein L has the same meaning as given for general formula (I), and a preferred range is also the same as given therefor; R has the same meaning as given for general formula (III), and a preferred range is also the same as given therefor; $Q_7$ has the same meaning as given for $Q_5$ in general formula (V), and a preferred range is also the same as given therefor; and n has the same meaning as given for general formula (VI), and a preferred range is also the same as given therefor.

Of the compounds represented by general formula (III), still further preferred are compounds represented by the following general formula (VIII):

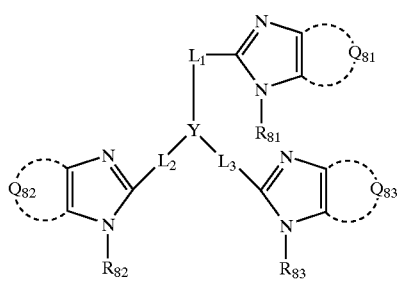

(VIII)

wherein $R_{81}$, $R_{82}$ and $R_{83}$ each has the same meaning as given for R in general formula (III), and a preferred range is also the same as given therefor; $Q_{81}$, $Q_{82}$ and $Q_{83}$ each has the same meaning as given for $Q_5$ in general formula (V), and a preferred range is also the same as given therefor; and $L_1$, $L_2$ and $L_3$ each has the same meaning as given for L in general formula (I).

$L_1$, $L_2$ and $L_3$ are each preferably a single bond, arylene, a divalent aromatic heterocycle or a connecting group comprising a combination thereof, more preferably a single bond, benzene, naphthalene, anthracene, pyridine, pyrazine, thiophene, furan, oxazole, thiazole, oxadiazole, thiadiazole, triazole or a connecting group comprising a combination thereof, still more preferably a single bond, benzene, thiophene or a connecting group comprising a combination thereof, particularly preferably a single bond, benzene or a connecting group comprising a combination thereof, and most preferably a single bond.

$L_1$, $L_2$ and $L_3$ may each have a constituent. As the substituents, the substituents of the heterocyclic groups represented by A in general formula (I) can be applied.

Y represents a nitrogen atom or a 1,3,5-benzenetriyl group, and the later may have substituents at positions 2, 4 and 6. Examples of the substituents include alkyl groups, aryl groups and halogen atoms. Y is preferably a nitrogen atom or an unsubstituted 1,3,5-benzenetriyl group, and more preferably an unsubstituted 1,3,5-benzenetriyl group.

Of the compounds represented by general formula (III), particularly preferred are compounds represented by the following general formula (IX):

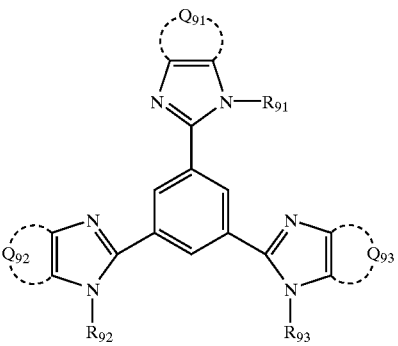

(IX)

wherein $R_{91}$, $R_{92}$ and $R_{93}$ each has the same meaning as given for R in general formula (III), and a preferred range is also the same as given therefor; and $Q_{91}$, $Q_{92}$ and $Q_{93}$ each has the same meaning as given for $Q_5$ in general formula (V), and a preferred range is also the same as given therefor.

Of the compounds represented by general formula (III), most preferred are compounds represented by the following general formula (X):

(X)

wherein $R_{101}$, $R_{102}$ and $R_{103}$ each has the same meaning as given for R in general formula (X), and a preferred range is also the same as given therefor; $R_{104}$, $R_{105}$ and $R_{106}$ each represents a substituent, the substituents of the heterocyclic groups represented by A in general formula (I) can be applied as the substituents, and preferred substituents are also the same as given therefor; and $p_1$, $p_2$ and $p_3$ each represents an integer of 0 to 3, preferably 0 to 2, more preferably 0 or 1, and still more preferably 0.

Next, general formula (XI) is described below. m and L each has the same meaning as given for general formula (I), and a preferred range is also the same as given therefor. $Q_3$ has the same meaning as given for general formula (III), and a preferred range is also the same as given therefor. $R_{11}$ represents a hydrogen atom or a substituent. Examples of the substituents represented by $R_{11}$ include the substituents for the heterocyclic groups represented by A in general formula (I).

The substituents represented by $R_{11}$ are preferably aliphatic hydrocarbon groups, aryl groups and aromatic heterocyclic groups; more preferably alkyl groups (each having preferably 1 to 20 carbon atoms, more preferably 1 to 12 carbon atoms and particularly preferably 1 to 8 carbon atoms, and including, for example, methyl, ethyl, iso-propyl, tert-butyl, n-octyl, n-decyl, n-hexadecyl, cyclopropyl, cyclopentyl and cyclohexyl), aryl groups (each having preferably 6 to 30 carbon atoms, more preferably 6 to 20 carbon atoms and particularly preferably 6 to 12 carbon atoms, and including, for example, phenyl, 2-methylphenyl, 3-methylphenyl, 4-methylphenyl, 4-methoxyphenyl, 3-trifluoromethylphenyl, pentafluorophenyl, 1-naphthyl and 2-naphthyl), and aromatic heterocyclic groups (preferably aromatic heterocyclic groups each having preferably 1 to 20 carbon atoms, more preferably 1 to 12 carbon atoms and still more preferably 2 to 10 carbon atoms, and more preferably aromatic heterocyclic groups each having at least one of nitrogen, oxygen, sulfur and selenium atoms, which include, for example, pyrrolidine, piperidine, pyrrole, furan, thiophene, imidazoline, imidazole, benzimidazole, naphthimidazole, thiazolidine, thiazole, benzthiazole, naphthothiazole, isothiazole, oxazoline, oxazole, benzoxazole, naphthoxazole, isoxazole, selenazole, benzoselenazole, naphthoselenazole, pyridine, quinoline, isoquinoline, indole, indolenine, pyrazole, pyrazine, pyrimidine, pyridazine, triazine, indazole, purine, phthalazine, naphthyridine, quinoxaline, quinazoline, cinnoline, pteridine, phenanthridine, phenanthroline, tetraazaindene and carbazole, preferably furan, thiophene, pyridine, quinoline, pyrazine, pyrimidine, pyridazine, triazine, phthalazine, naphthyridine, quinoxaline and quinazoline, more preferably furan, thiophene, pyridine and quinoline, and still more preferably quinoline); and more preferably aryl groups and aromatic heterocyclic groups. The substituents represented by $R_{11}$ may be further substituted, and may connect to form rings if possible.

Of the compounds represented by general formula (XI), more preferred are compounds represented by the following general formula (XII):

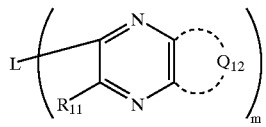

(XII)

wherein m and L each has the same meaning as given for general formula (I), and a preferred range is also the same as given therefor; $Q_{12}$ has the same meaning as given for $Q_4$ in general formula (IV), and a preferred range is also the same as given therefor; and $R_{11}$ has the same meaning as given for general formula (XI), and a preferred range is also the same as given therefor.

Of the compounds represented by general formula (XI), still more preferred are compounds represented by the following general formula (XIII):

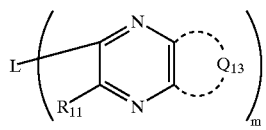

(XIII)

wherein m and L each has the same meaning as given for general formula (I), and a preferred range is also the same as given therefor; $Q_{13}$ has the same meaning as given for $Q_5$ in general formula (V), and a preferred range is also the same as given therefor; and $R_{11}$ has the same meaning as given for general formula (XI), and a preferred range is also the same as given therefor. of the compounds represented by general formula (XI), particularly preferred are compounds represented by the following general formula (XIV):

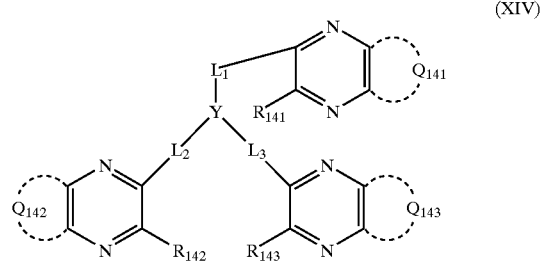

(XIV)

wherein $L_1$, $L_2$, $L_3$ and Y each has the same meaning as given for general formula (VIII), and a preferred range is also the same as given therefor; $Q_{141}$, $Q_{142}$ and $Q_{143}$ each has the same meaning as given for $Q_5$ in general formula (V), and a preferred range is also the same as given therefor; and $R_{141}$, $R_{142}$ and $R_{143}$ each has the same meaning as given for $R_{11}$ in general formula (XI), and a preferred range is also the same as given therefor.

Of the compounds represented by general formula (XI), most preferred are compounds represented by the following general formula (XV):

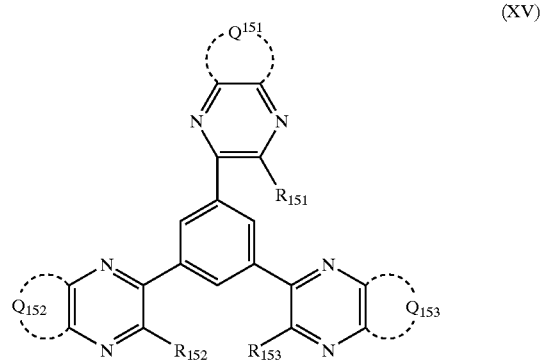

(XV)

wherein $Q_{151}$, $Q_{152}$ and $Q_{153}$ each has the same meaning as given for $Q_5$ in general formula (V), and a preferred range is also the same as given therefor; and $R_{151}$, $R_{152}$ and $R_{153}$ each has the same meaning as given for $R_{11}$ in general formula (XI), and a preferred range is also the same as given therefor.

Specific examples of the compounds of the invention represented by general formula (I) are shown below, but it is to be understood that the invention is not limited thereto.

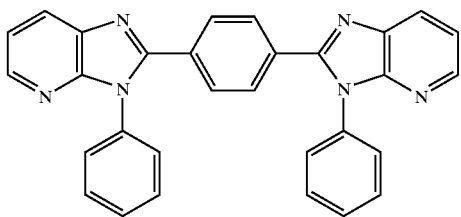
1
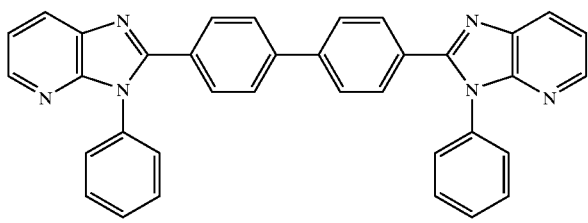
2
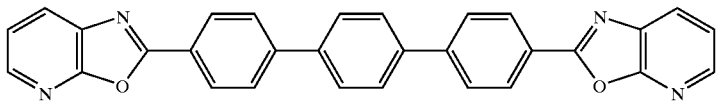
3
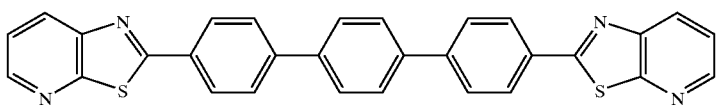
4
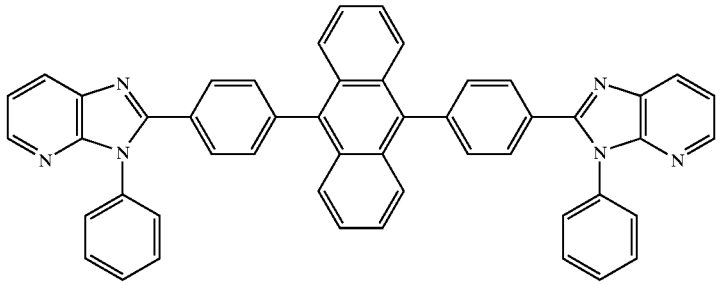
5
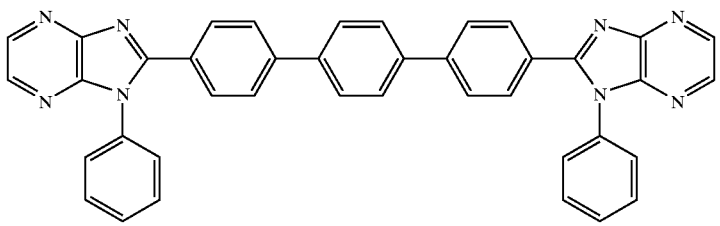
6
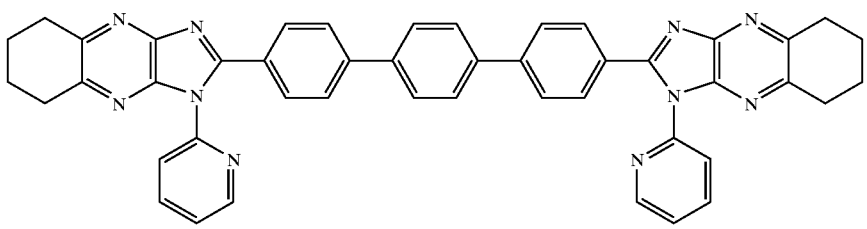
7

-continued
8
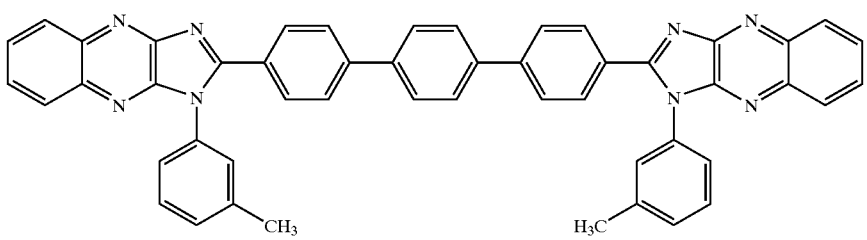
9
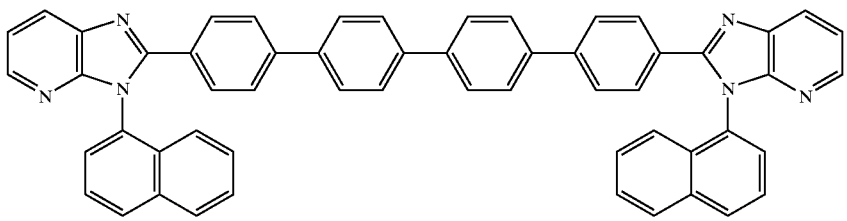
10
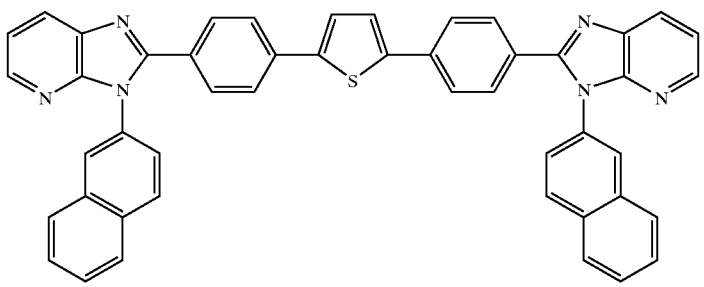
11
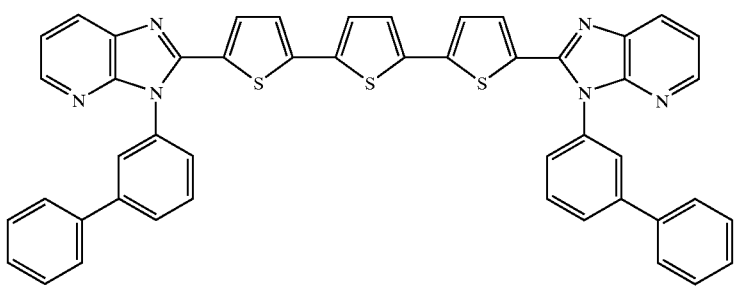
12
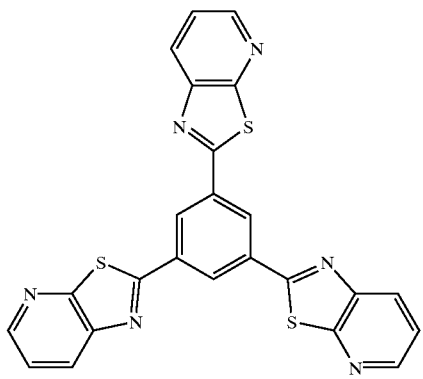
13
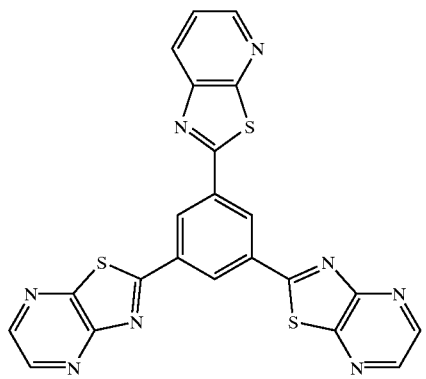

-continued
14
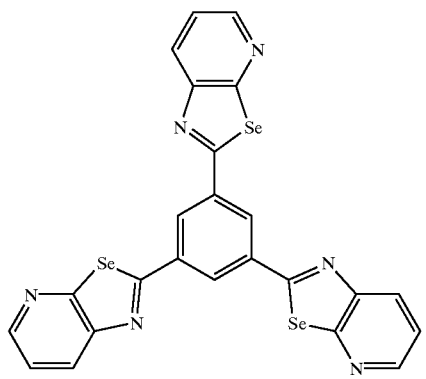
15
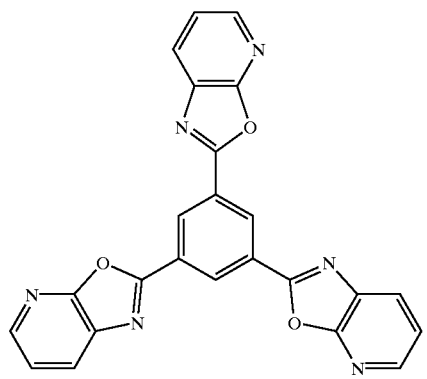
16
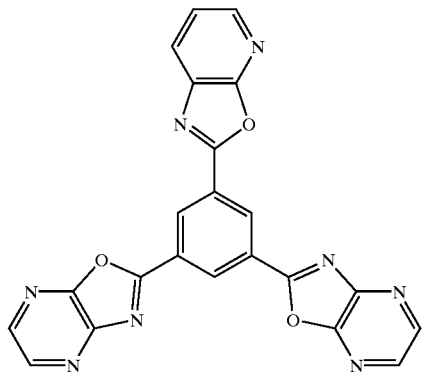
17
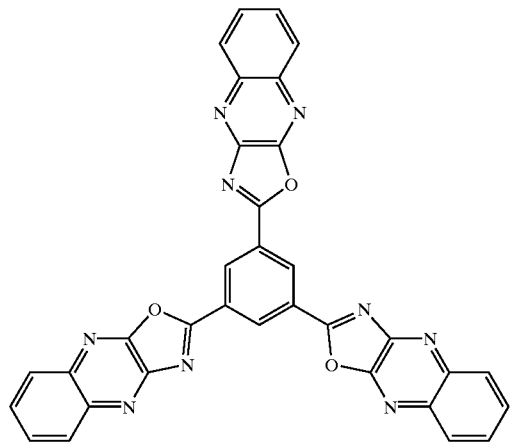
18
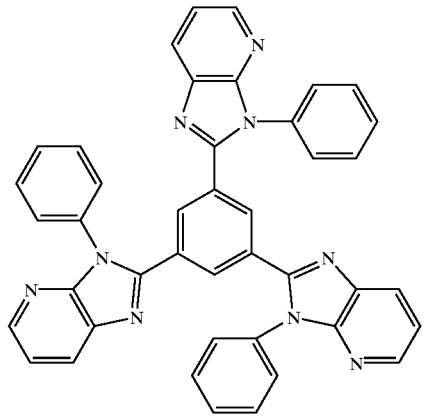
19
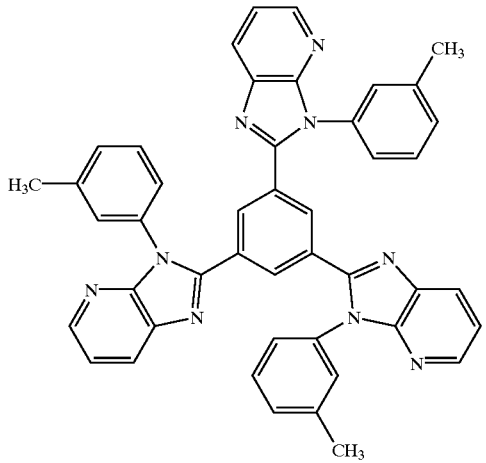

-continued
20
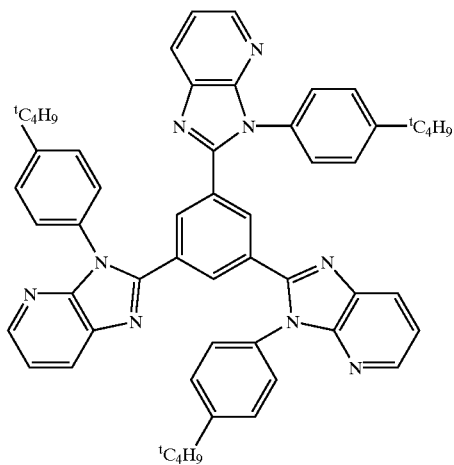
21
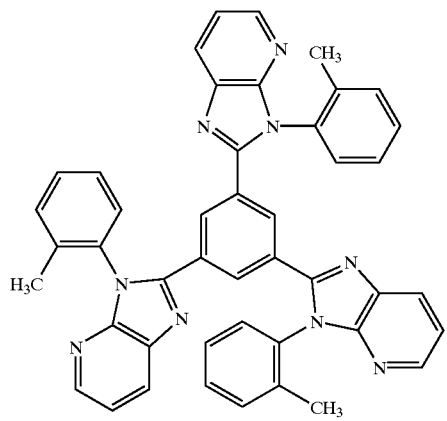
22
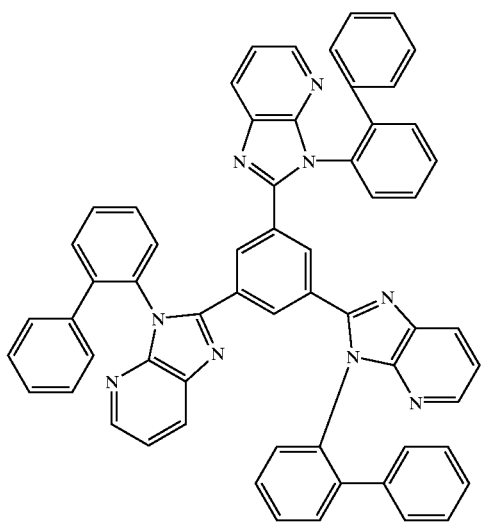
23
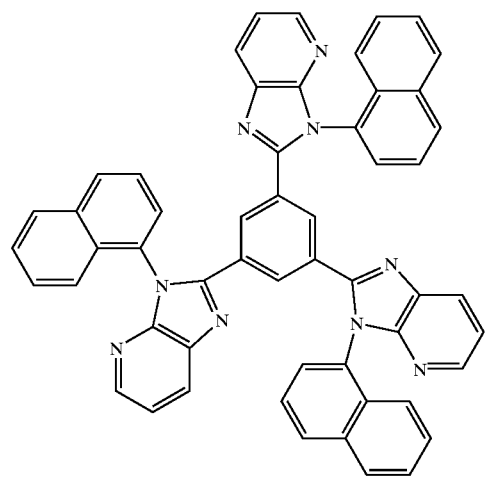
24
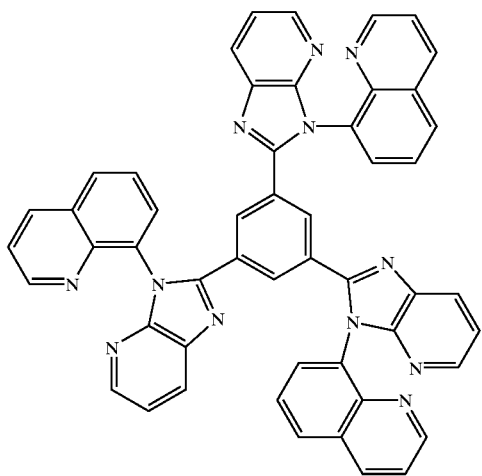
25
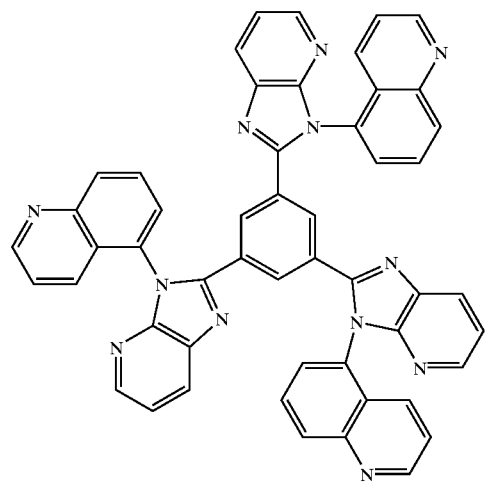

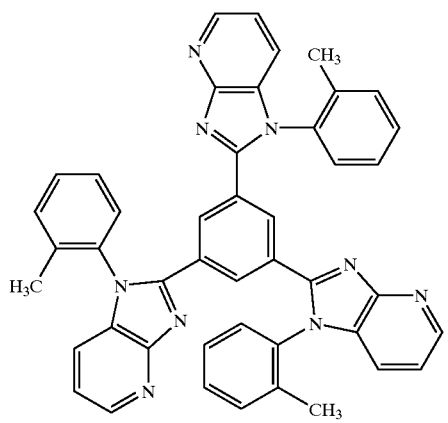
26
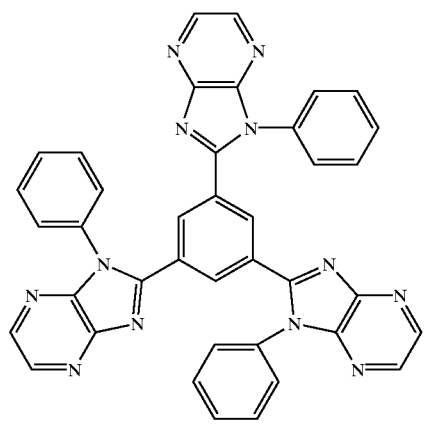
27
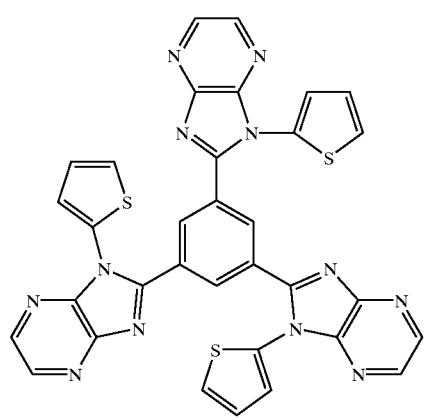
28
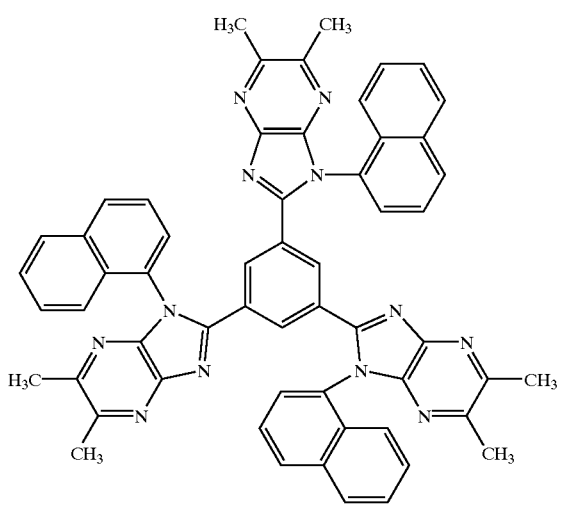
29
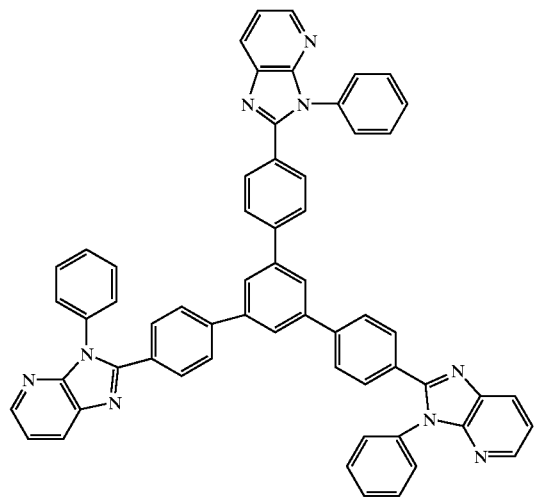
30
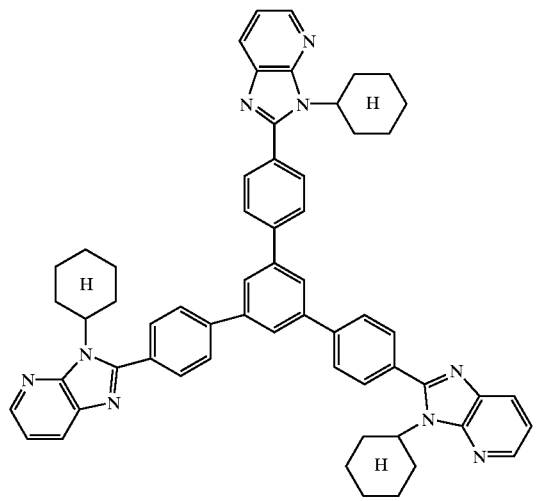
31

-continued
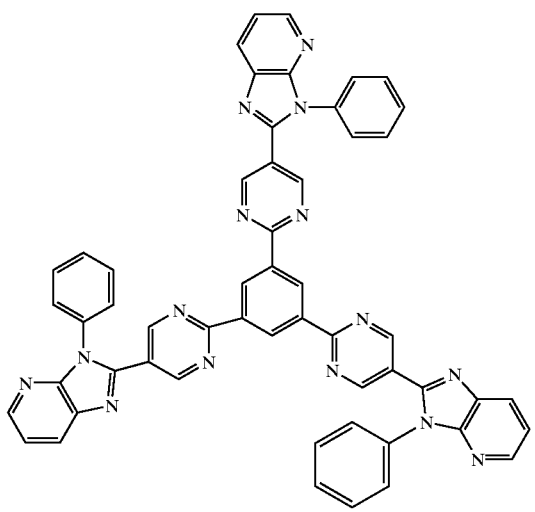
32
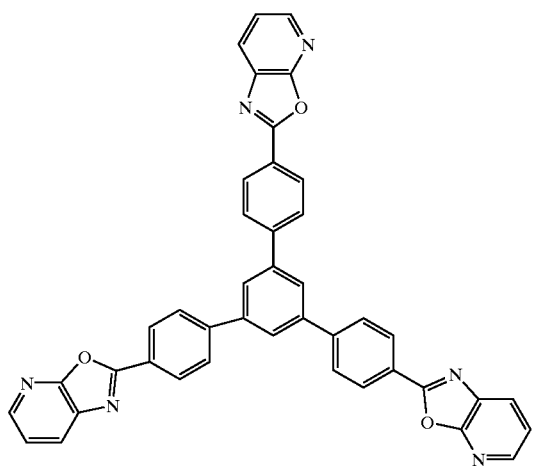
33
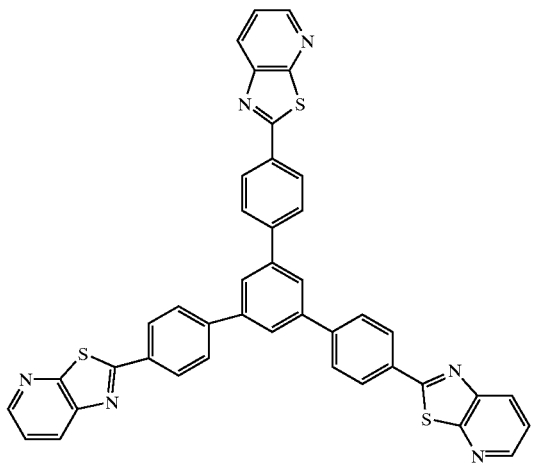
34
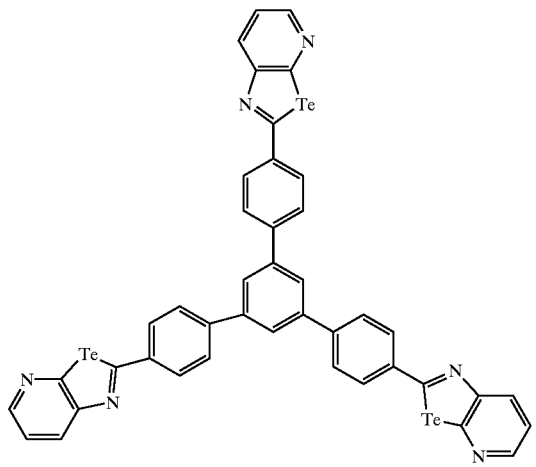
35
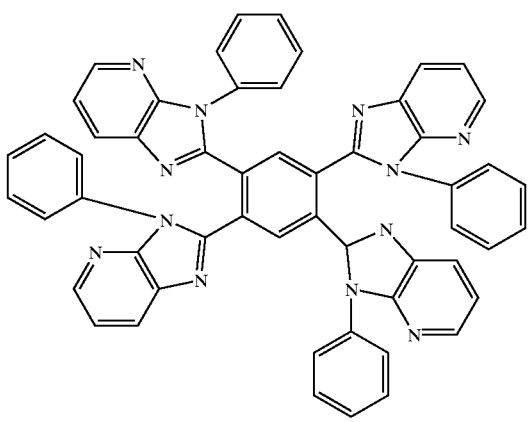
36
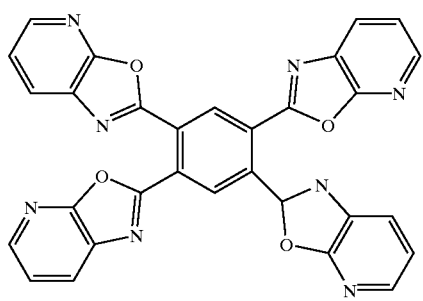
37

38
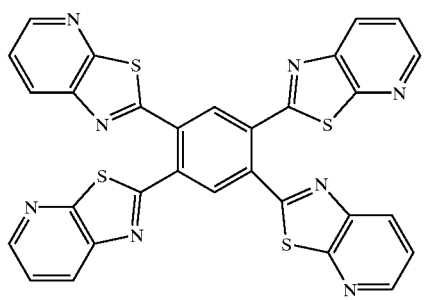
39
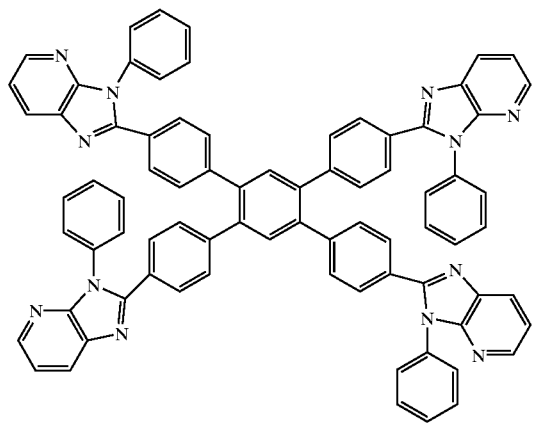
40
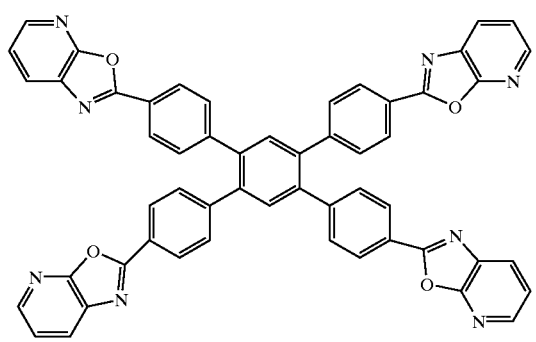
41
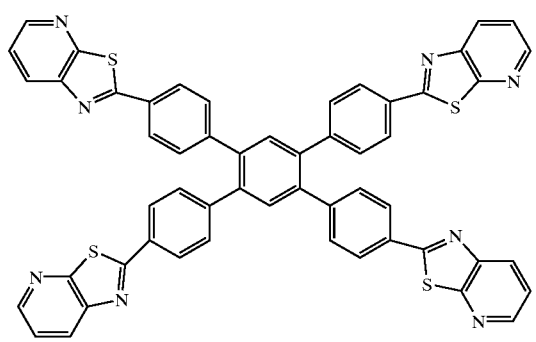
42
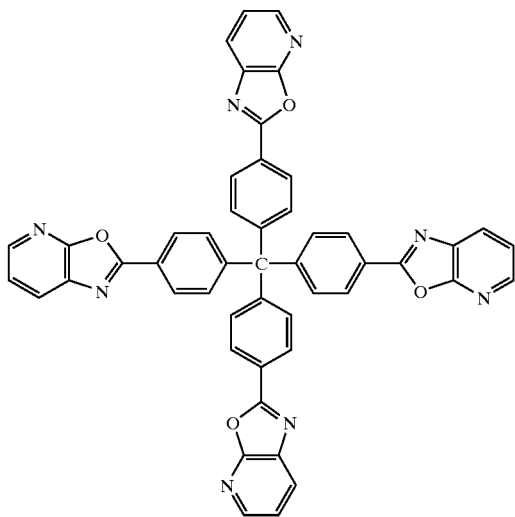
43
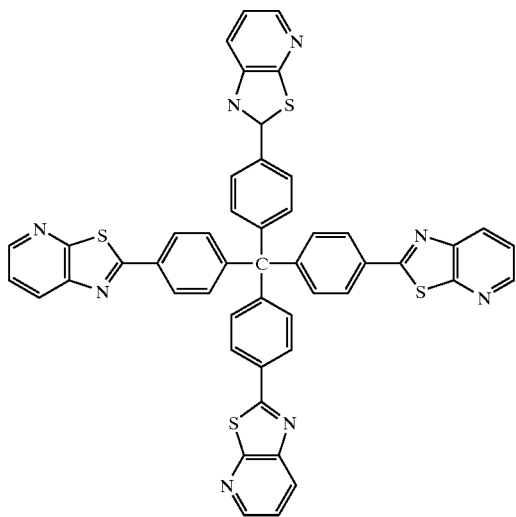

44
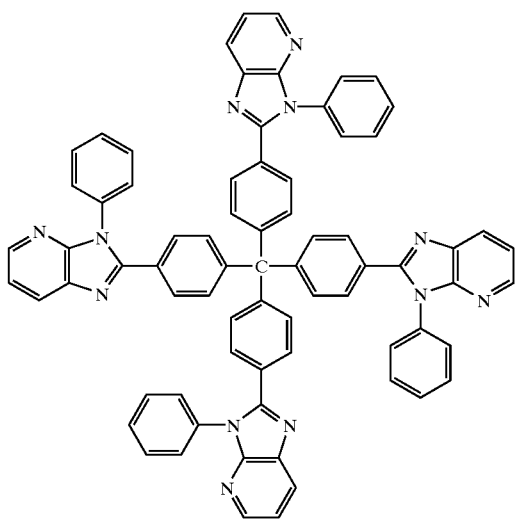
45
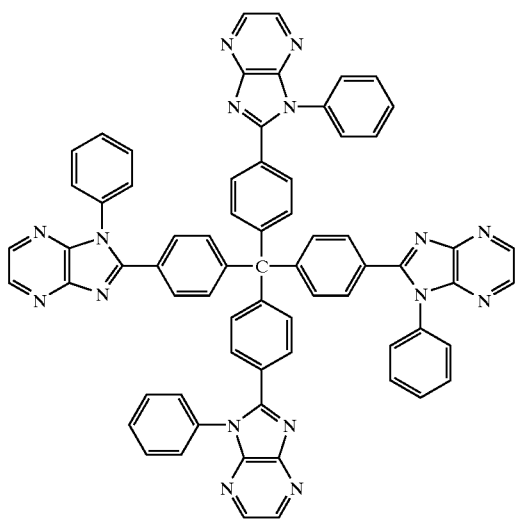
46
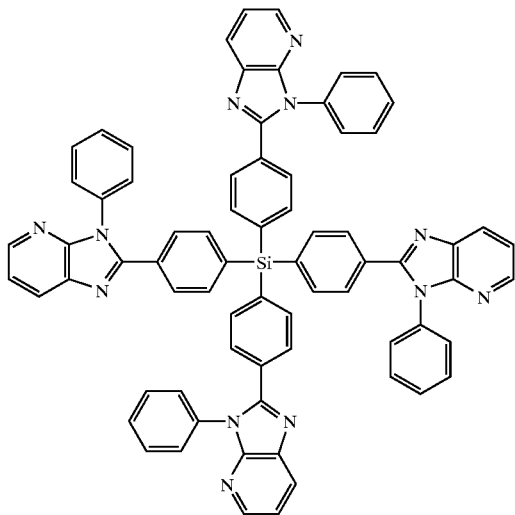
47
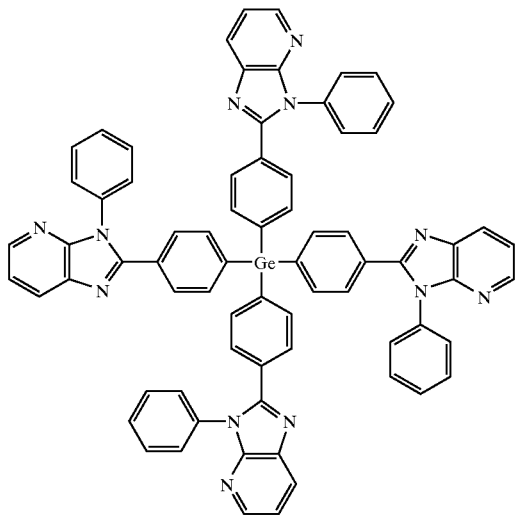
48
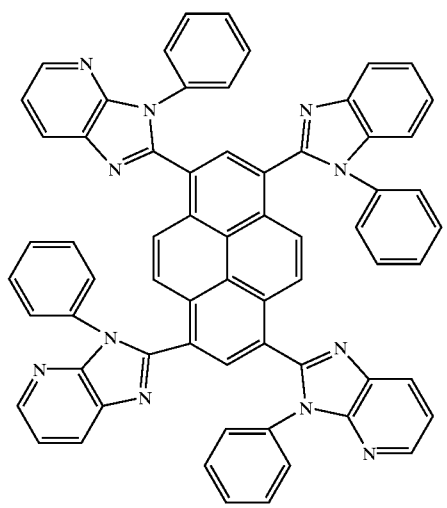
49
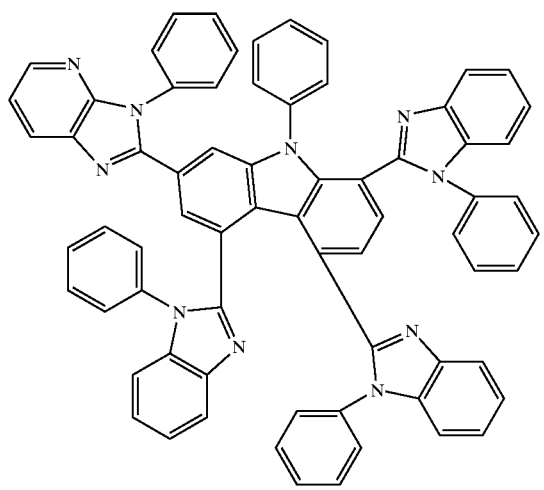

-continued
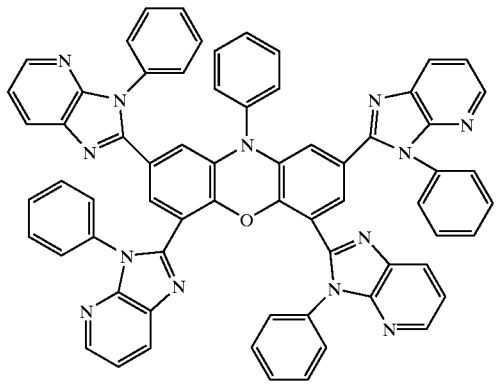
50
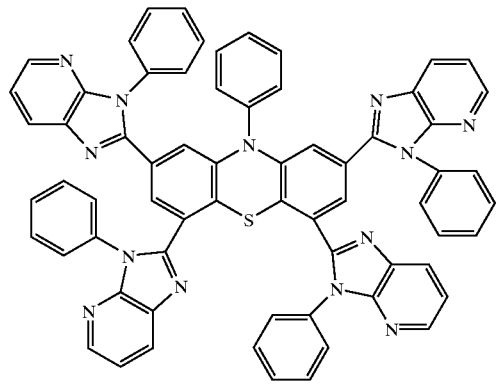
51
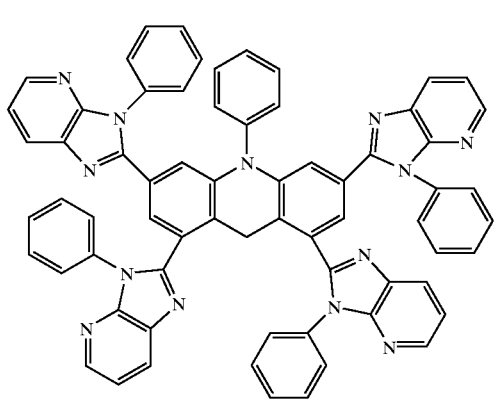
52
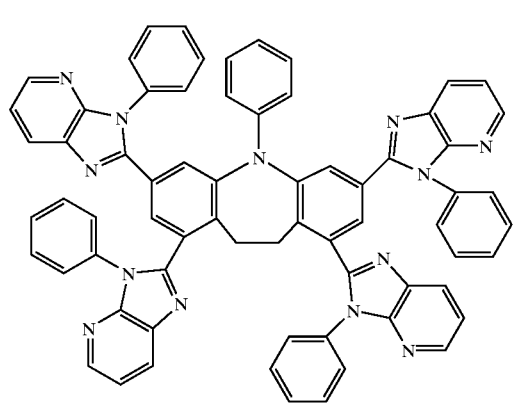
53
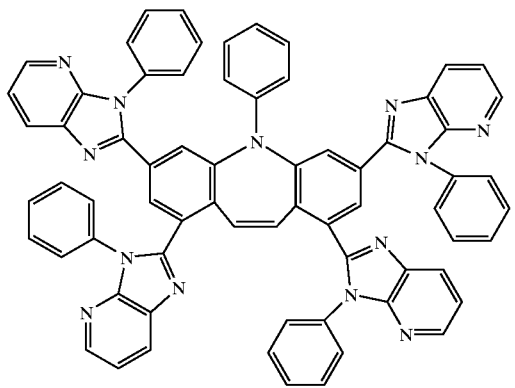
54
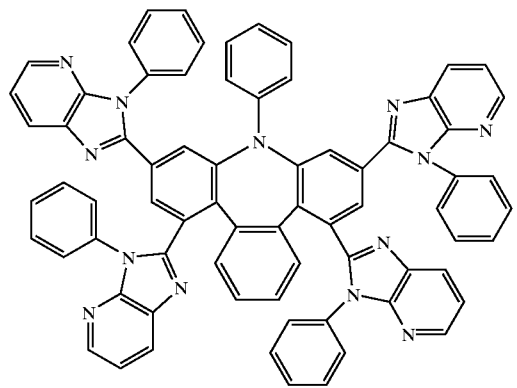
55
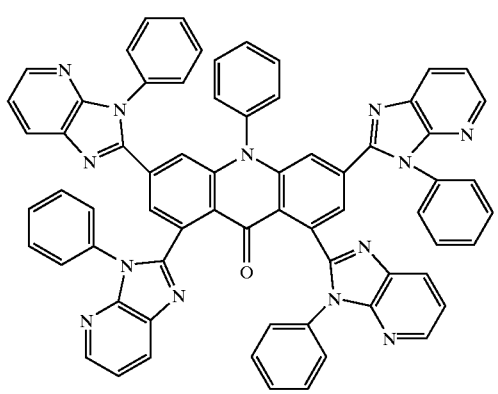
56
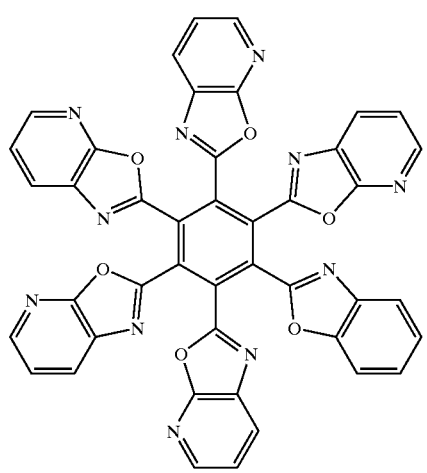
57

-continued
58
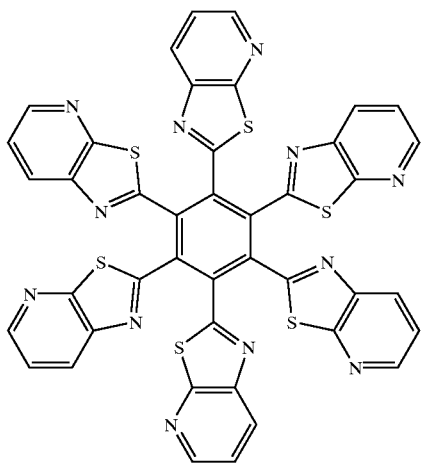
59
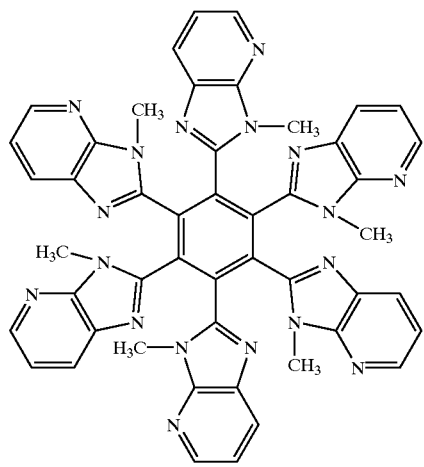
60
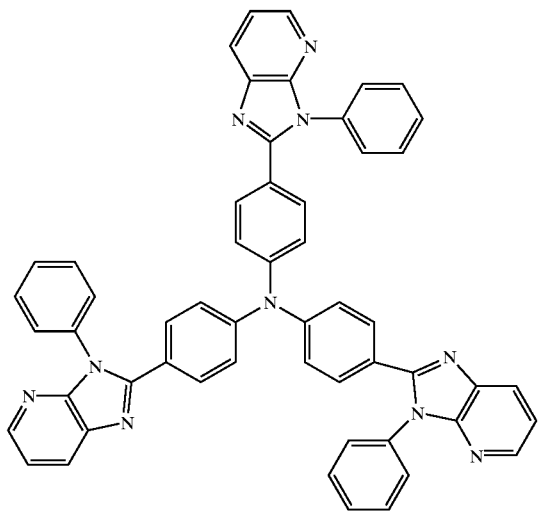
61
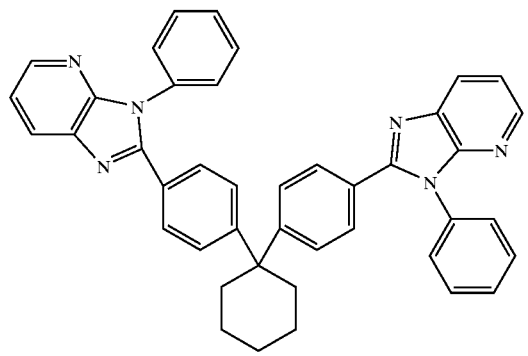
62
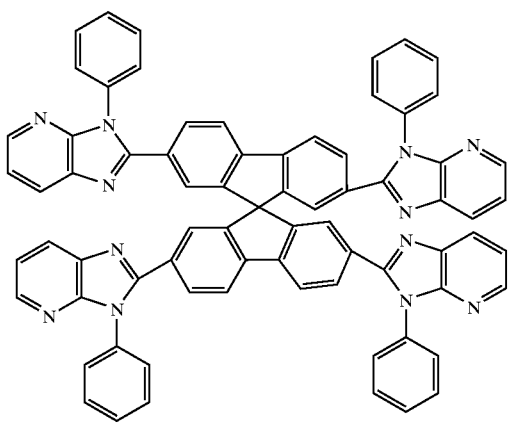
63
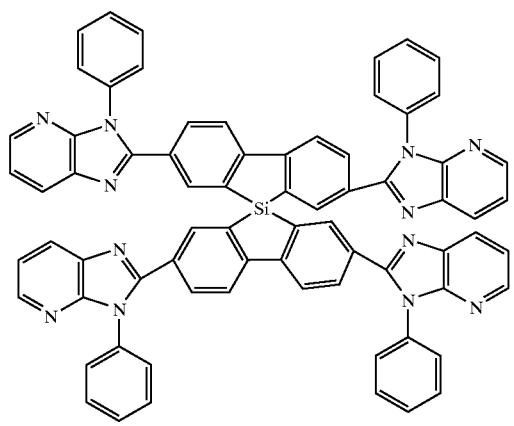

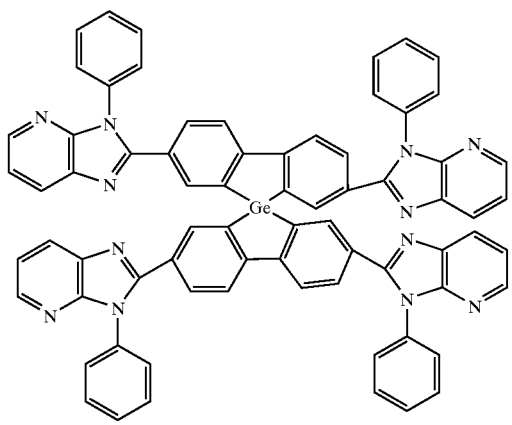
64
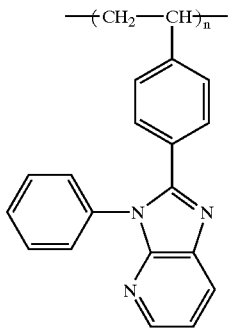
65
Mass-average molecular weight: 16,500
(in terms of polystyrene)
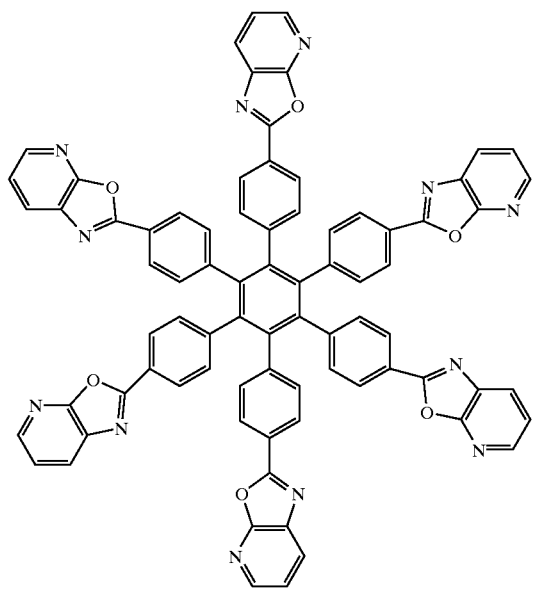
66
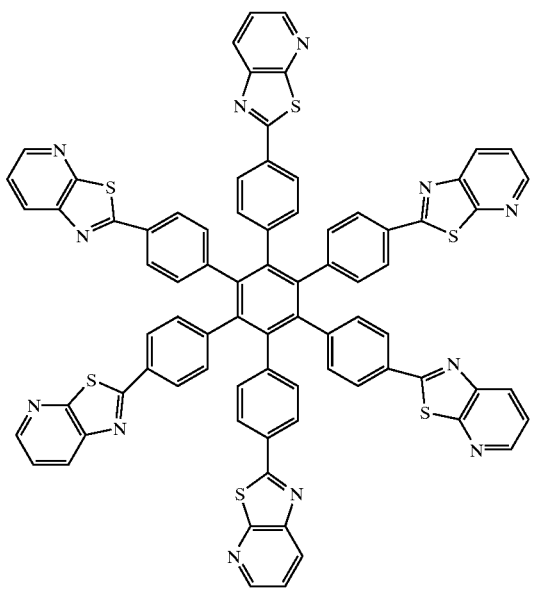
67
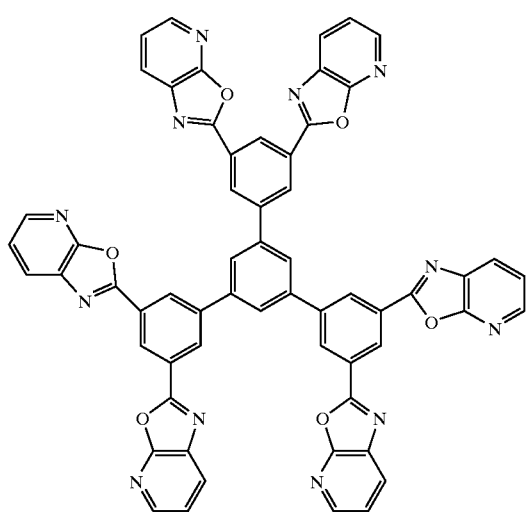
68
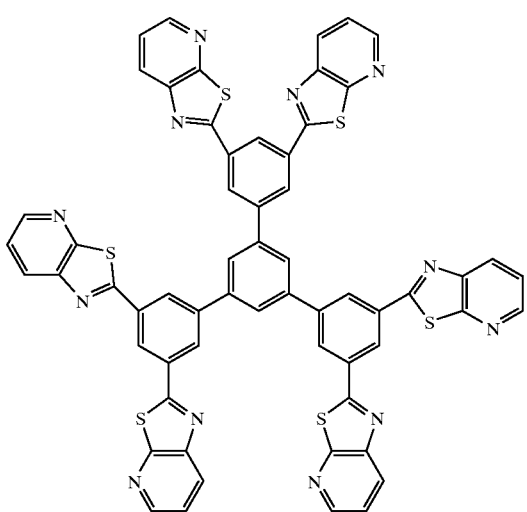
69

70
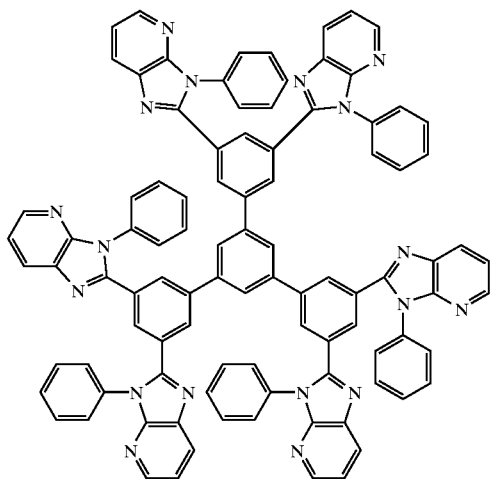
71
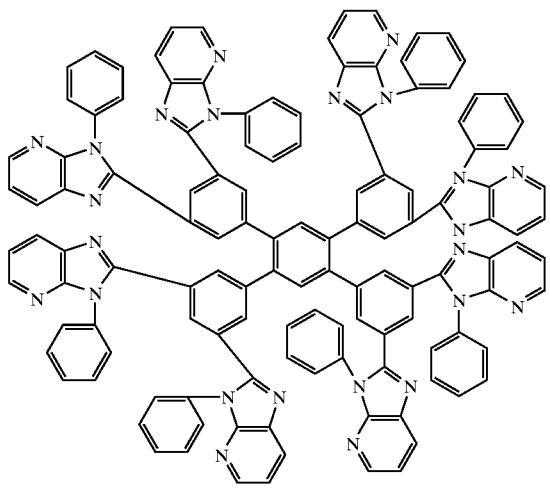
72
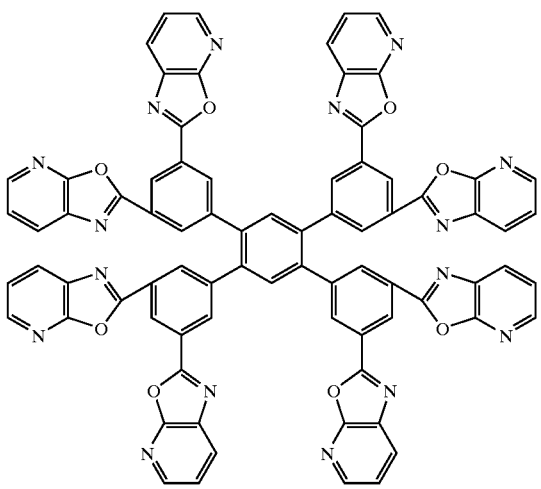
73
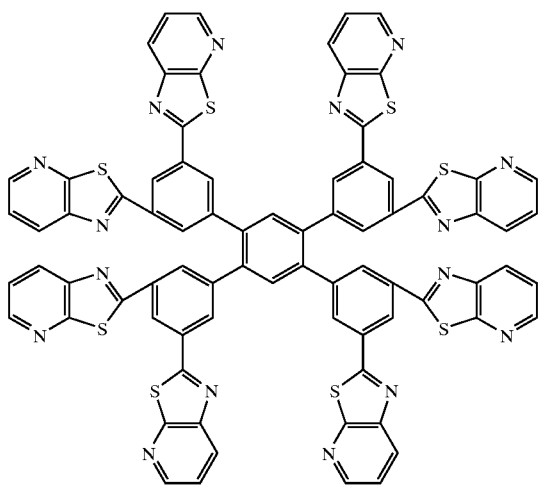
74
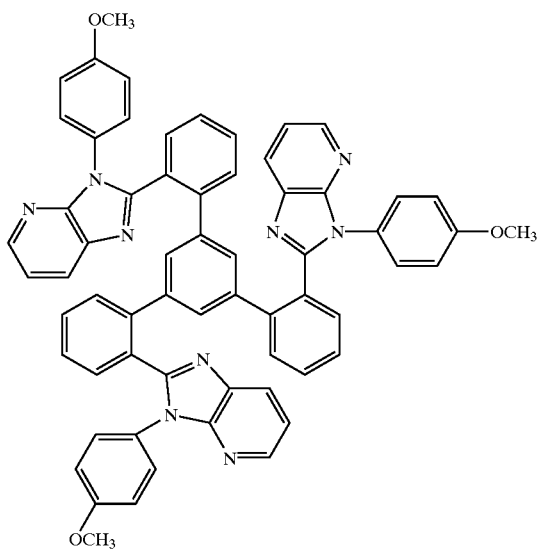
75
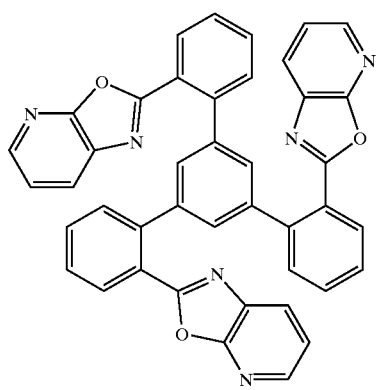

76
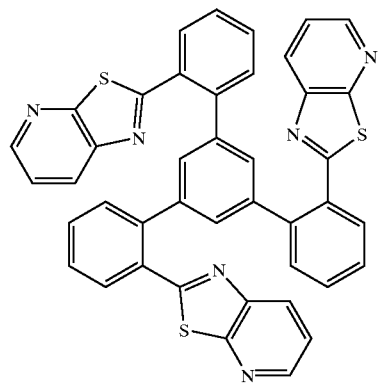
77
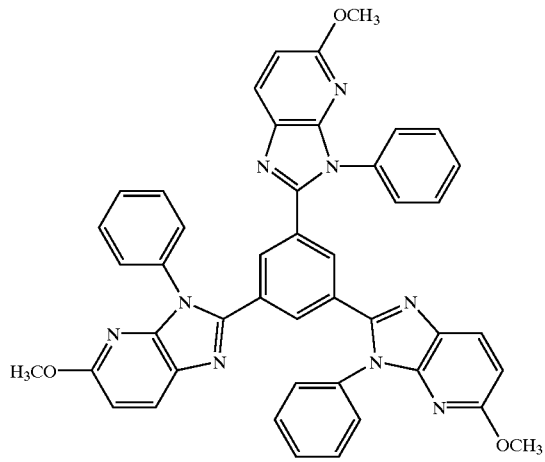
78
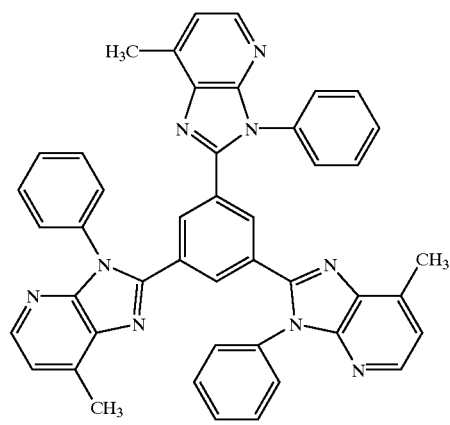
79
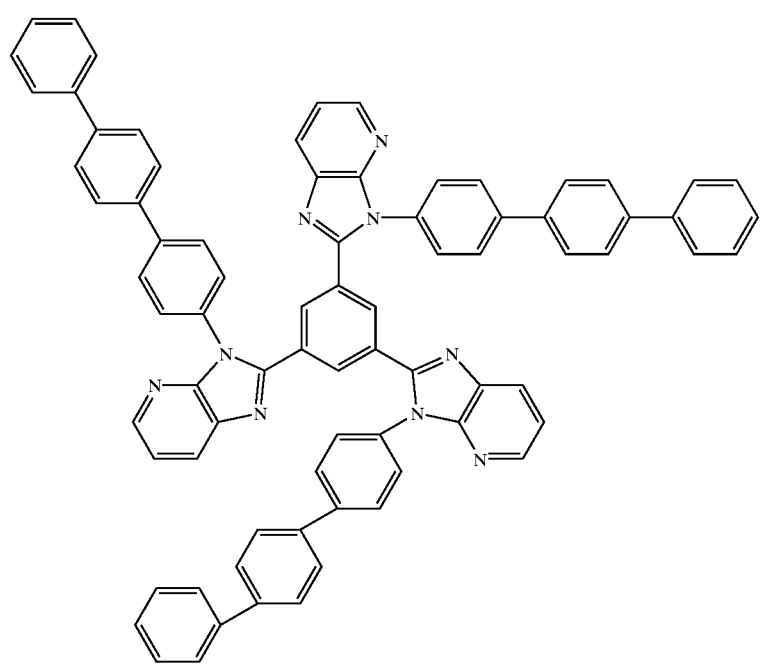

-continued
80
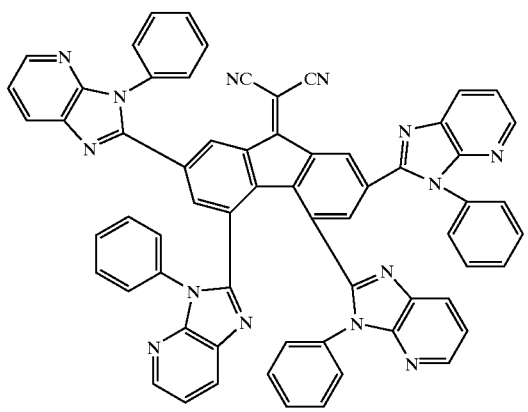
81
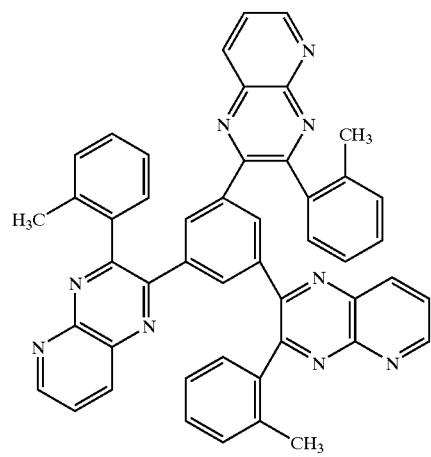
82
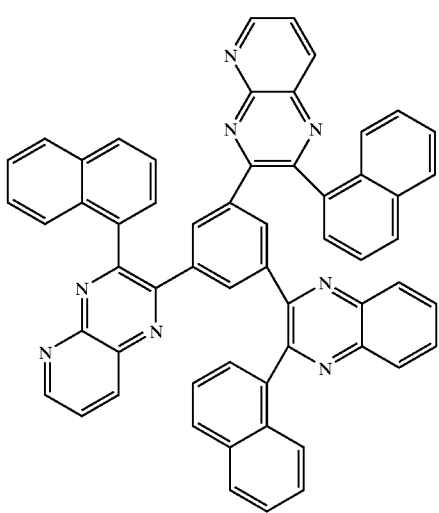
83
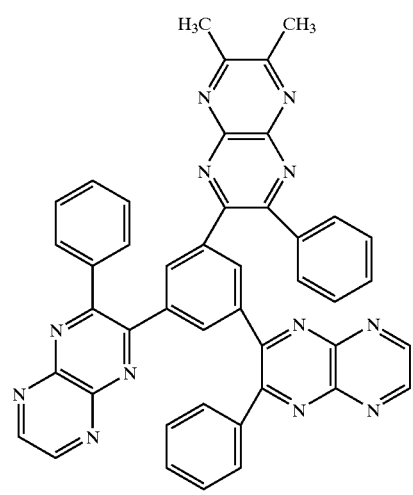
84
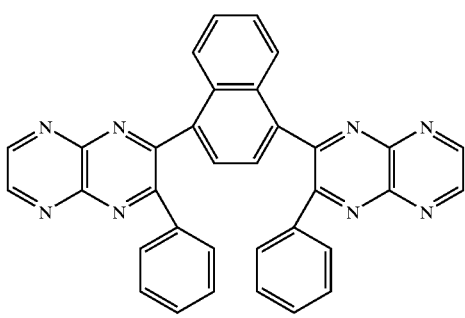
85
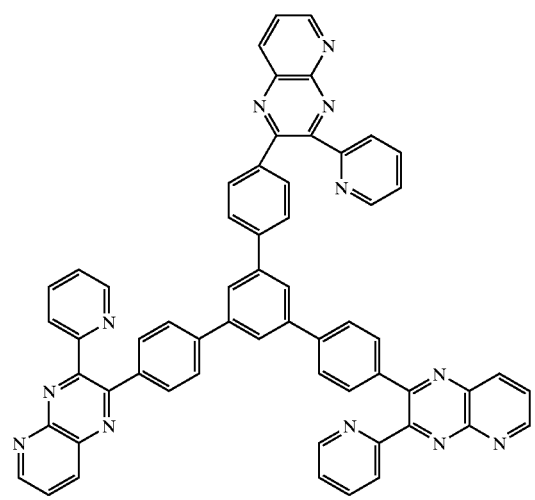

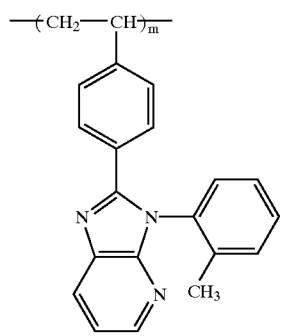
86
Mass-average molecular weight: 21,000
(in terms of polystyrene)
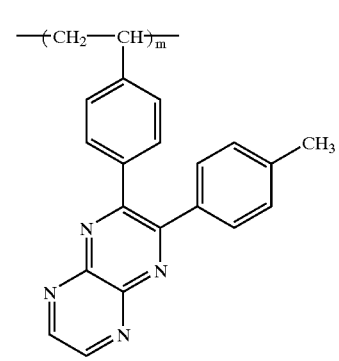
87
Mass-average molecular weight: 14,000
(in terms of polystyrene)
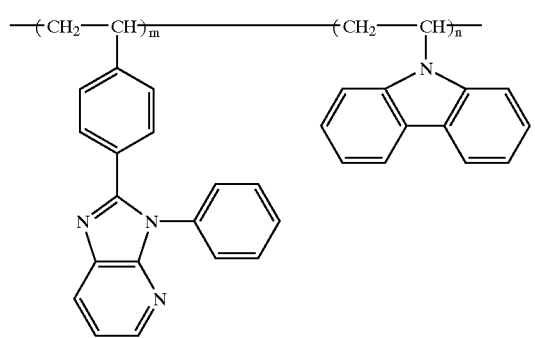
88
Mass-average molecular weight: 17,000
(in terms of polystyrene)
m:n = 1:1 (by mol)
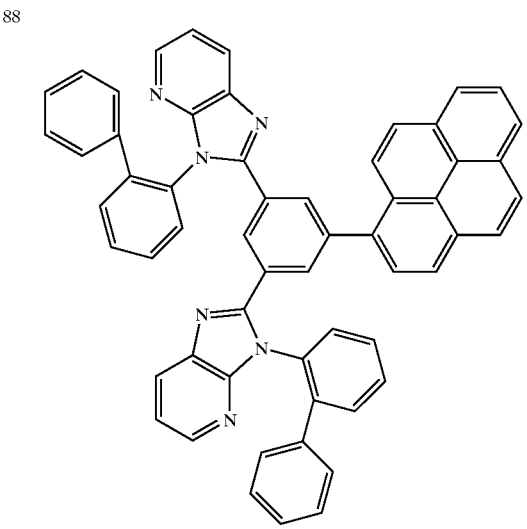
89
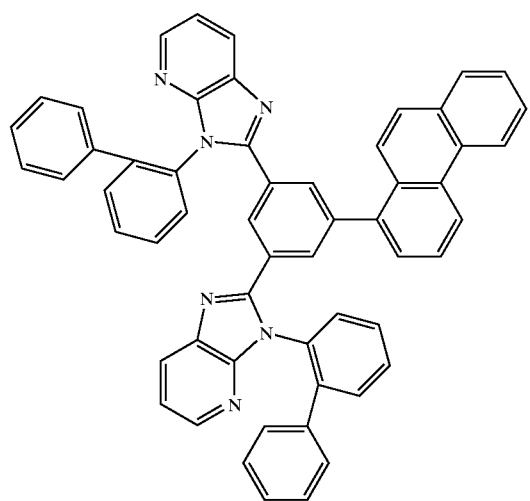
90
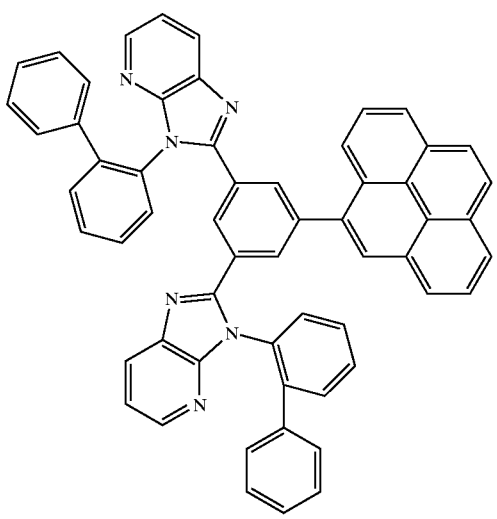
91

-continued
92
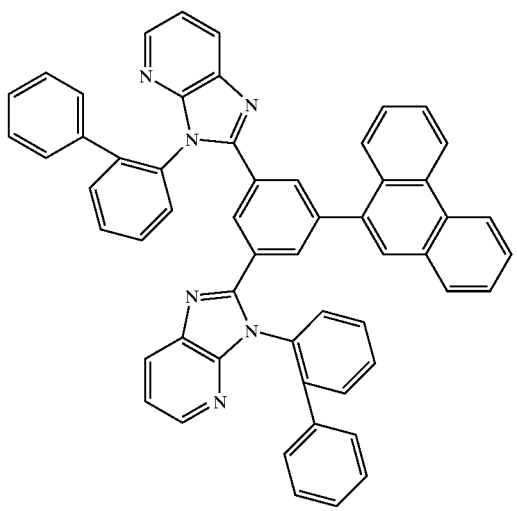
93
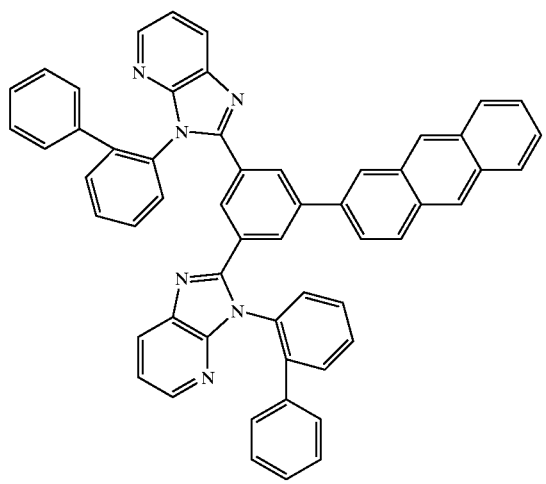
94
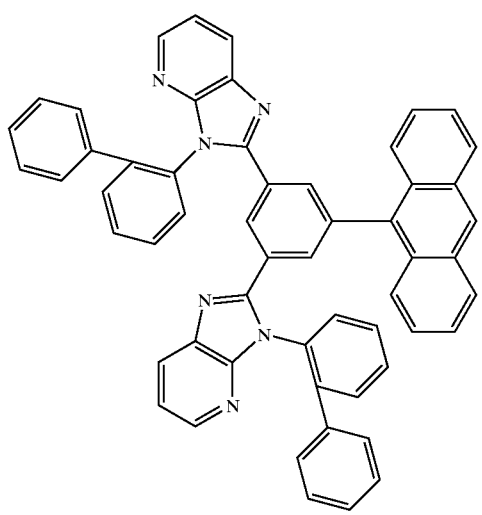
95
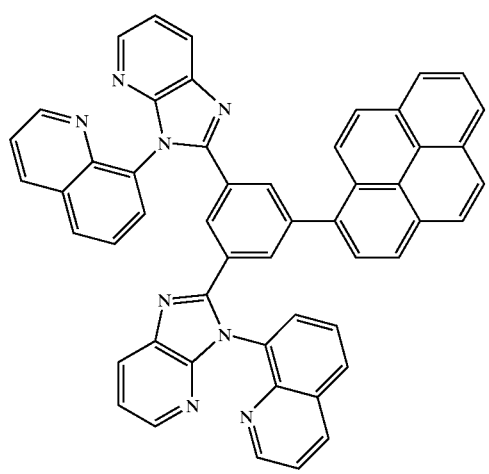
96
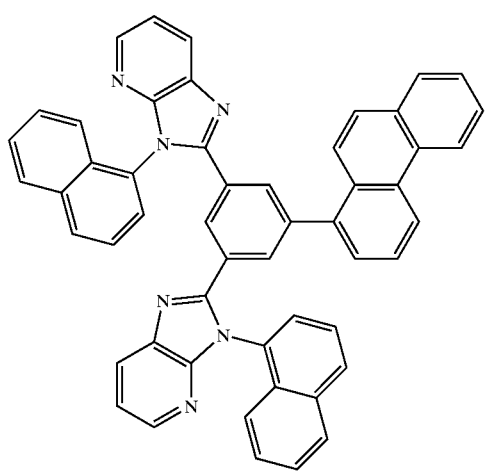
97
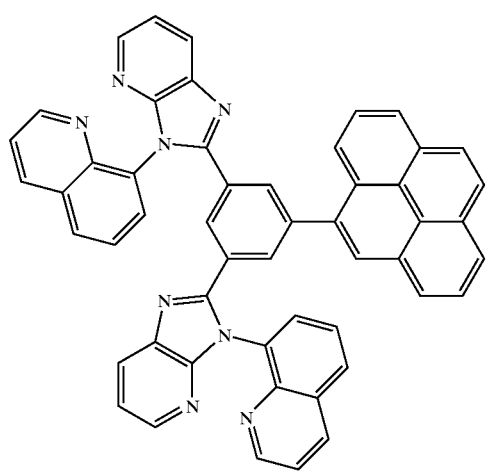

98
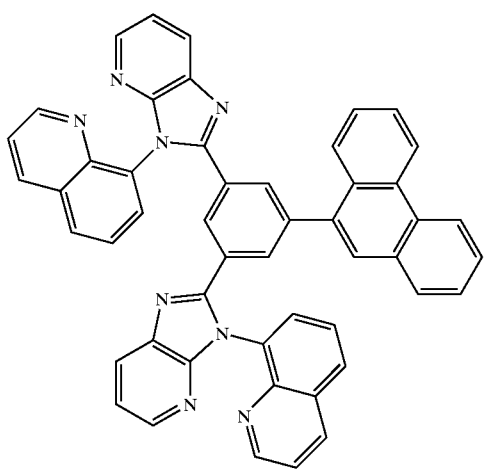
99
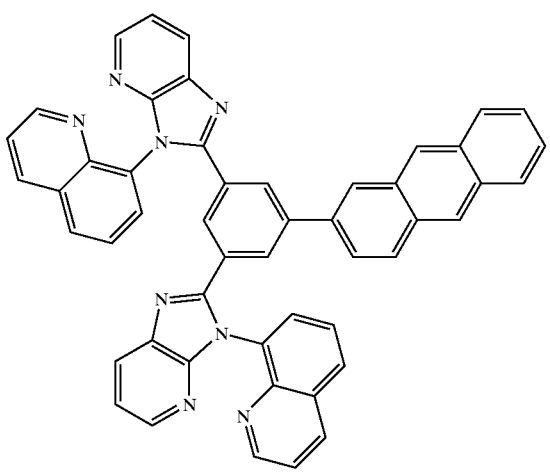
100
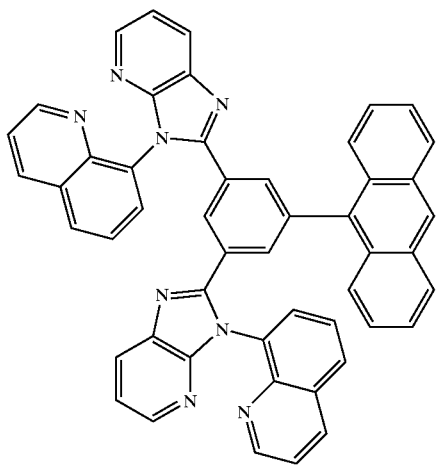
101
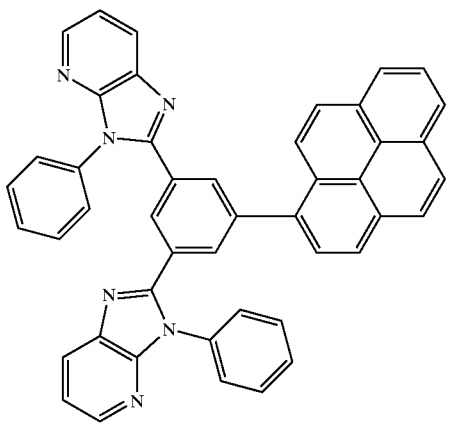
102
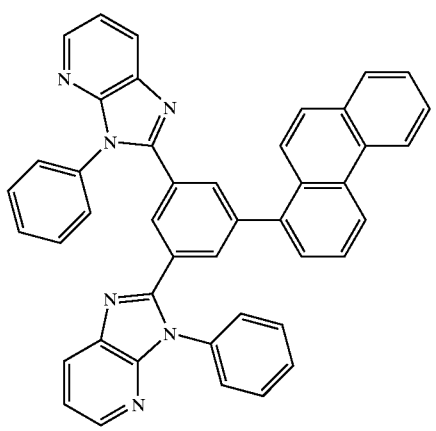
103
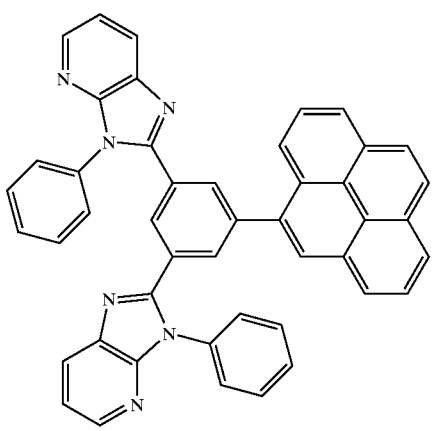

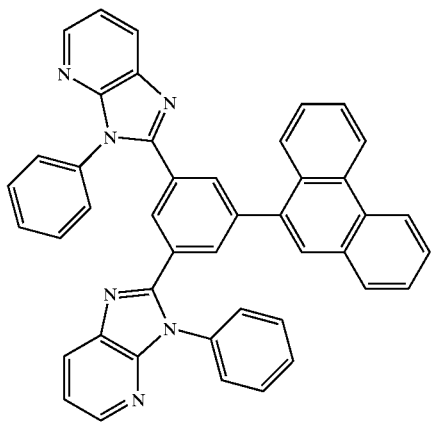
104
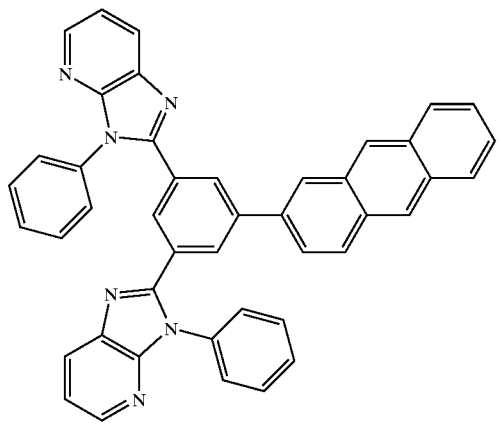
105
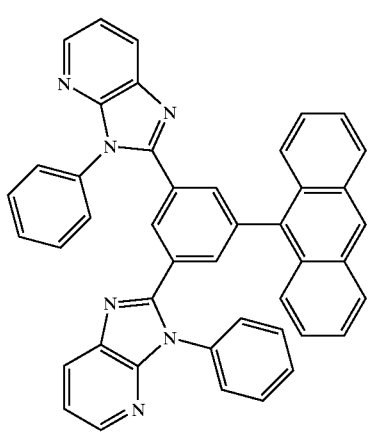
106
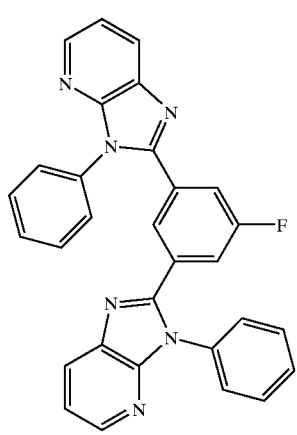
107
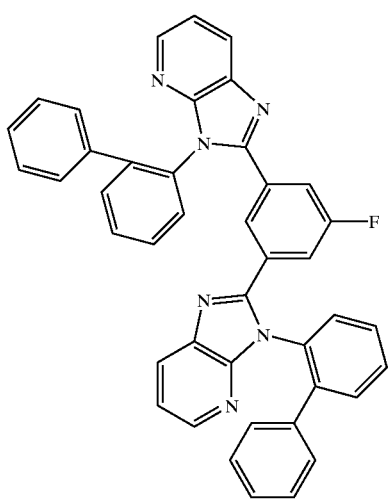
108
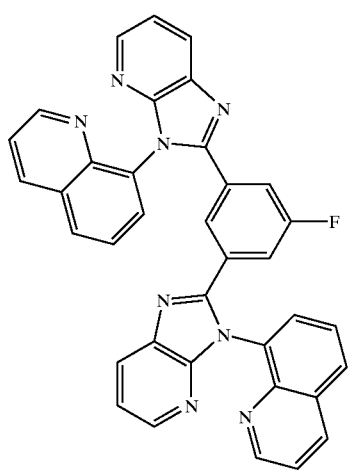
109

-continued
110
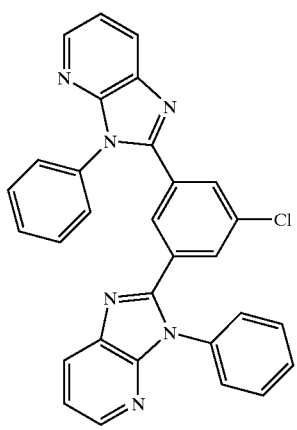
111
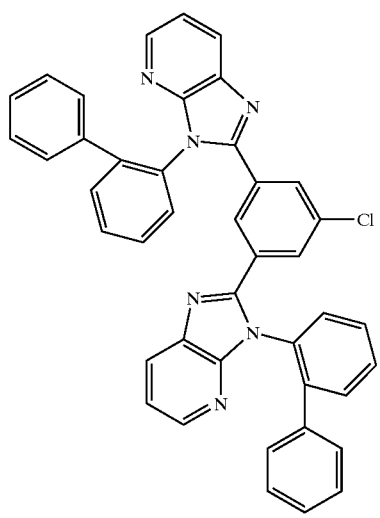
112
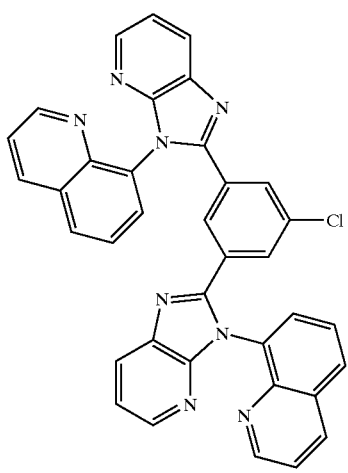
113
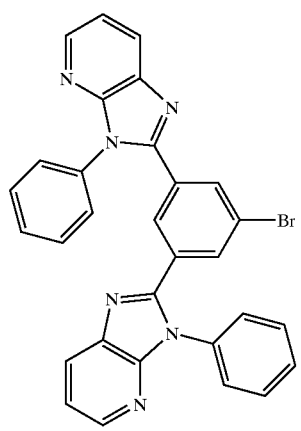
114
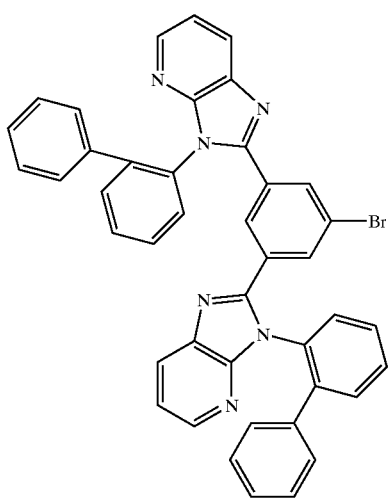
115
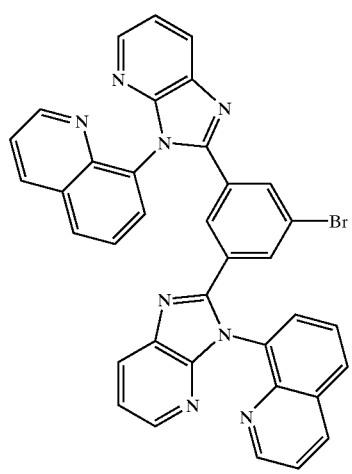

-continued

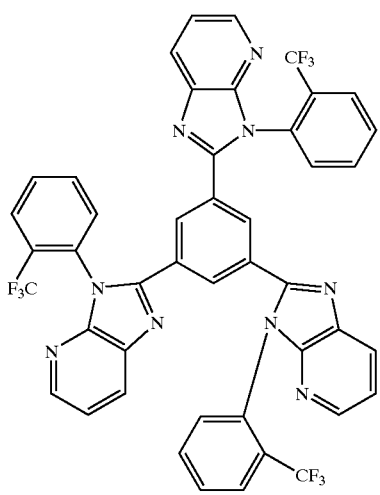
116

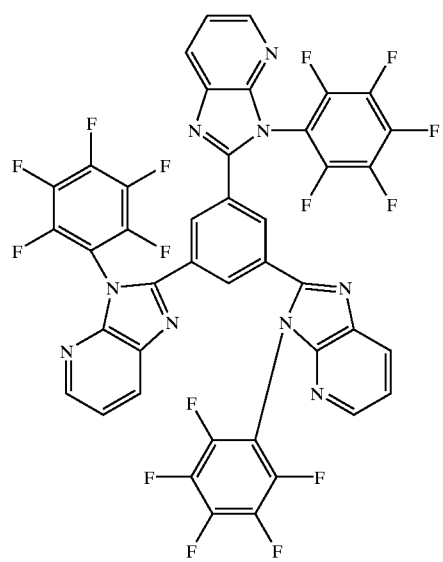
117

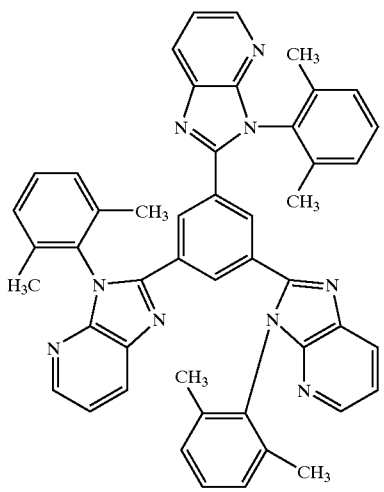
118

The compounds of the invention represented by general formulas (I) to (XV) can be synthesized with reference to methods described in JP-B-44-23025 (the term "JP-B" as used herein means an "examined Japanese patent publication"), JP-B-48-8842, JP-A-53-6331, JP-A-10-92578, U.S. Pat. Nos. 3,449,255 and 5,766,779, *J. Am. Chem. Soc.*, 94, 2414 (1972), *Helv. Chim. Acta*, 63, 413 (1980) and Liebigs Ann. Chem., 1423 (1982).

Synthesis methods of the compounds of the invention are specifically illustrated below.

Synthesis Example 1

Synthesis of Exemplified Compound 2

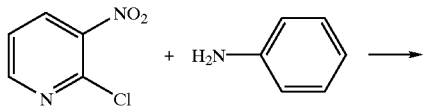

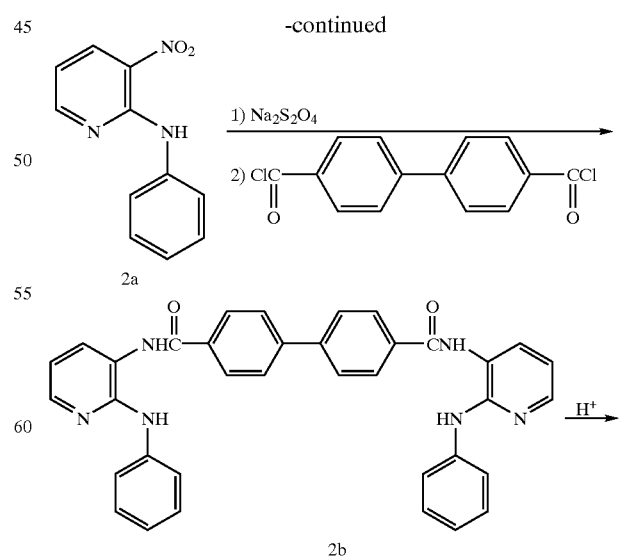

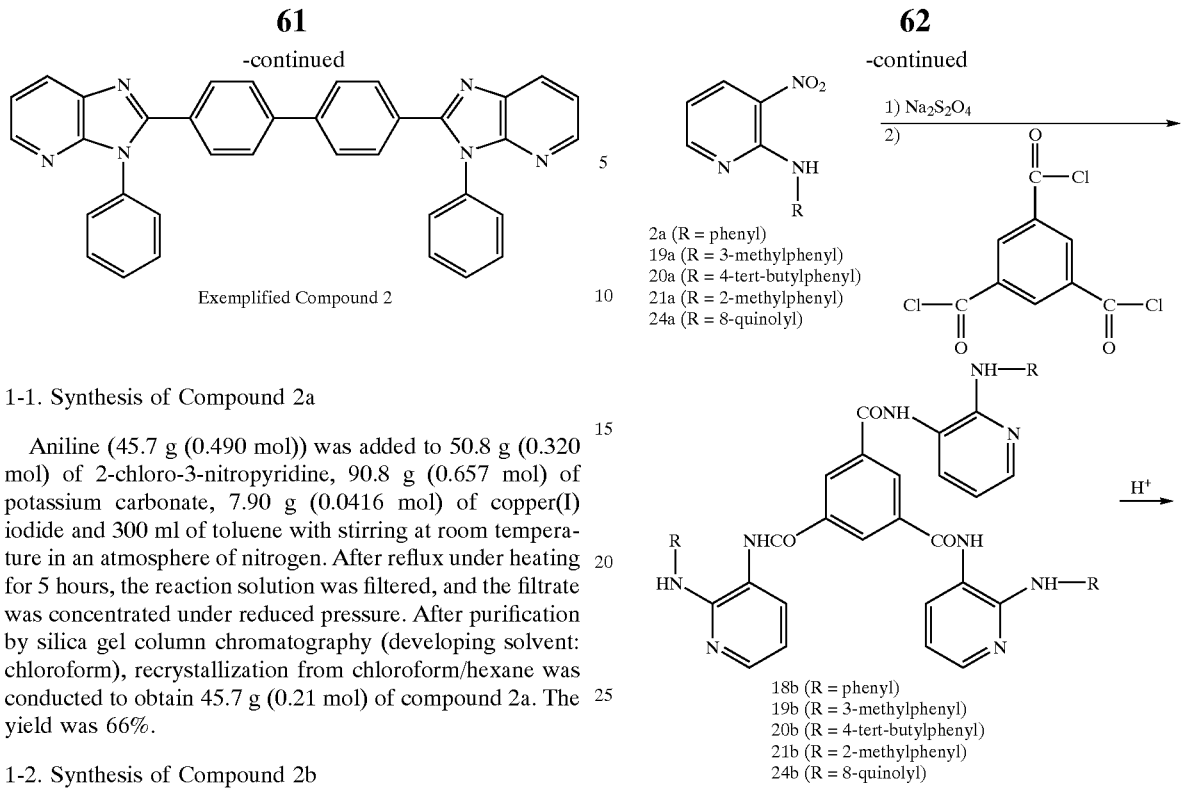

Exemplified Compound 2

1-1. Synthesis of Compound 2a

Aniline (45.7 g (0.490 mol)) was added to 50.8 g (0.320 mol) of 2-chloro-3-nitropyridine, 90.8 g (0.657 mol) of potassium carbonate, 7.90 g (0.0416 mol) of copper(I) iodide and 300 ml of toluene with stirring at room temperature in an atmosphere of nitrogen. After reflux under heating for 5 hours, the reaction solution was filtered, and the filtrate was concentrated under reduced pressure. After purification by silica gel column chromatography (developing solvent: chloroform), recrystallization from chloroform/hexane was conducted to obtain 45.7 g (0.21 mol) of compound 2a. The yield was 66%.

1-2. Synthesis of Compound 2b

A solution of 69.0 g (0.396 mol) of sodium hydrosulfite in 220 ml of water was added dropwise to a solution of 17.0 g (0.0790 mol) of compound 2a in 170 ml of tetrahydrofuran with stirring at room temperature in an atmosphere of nitrogen. After stirring for 1 hour, 170 ml of ethyl acetate was added, and then, a solution of 13.6 g (0.162 mol) of sodium hydrogencarbonate in 140 ml of water was added dropwise. Further, a solution of 10.0 g (0.0358 mol) of 4,4'-biphenyldicarbonyl chloride in 100 ml of ethyl acetate was added dropwise, followed by stirring at room temperature for 5 hours. A solid precipitated was taken by filtration, and washed with water and subsequently with ethyl acetate, thereby obtaining 16.0 g (0.0277 mol) of compound 2b. The yield was 77%.

1-3. Synthesis of Exemplified Compound 2

Xylene (300 ml) was added to 10.0 g (0.0173 mol) of compound 2b and 2.3 g (0.0121 mol) of p-toluenesulfonic acid monohydrate, and the resulting solution was refluxed under heating for 6 hours in an atmosphere of nitrogen to conduct azeotropic dehydration. Then, a solid precipitated was taken by filtration, and recrystallized from dimethylformamide/acetonitrile, thereby obtaining 5.20 g (9.62 mmol) of exemplified compound 2. The yield was 57%, and the melting point was from 298° C. to 300° C.

Synthesis Example 2

Synthesis of Exemplified Compound 18

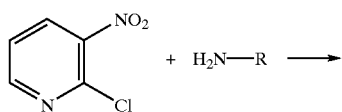

Exemplified Compound 18 (R=phenyl)
Exemplified Compound 19 (R=3-methylphenyl)
Exemplified Compound 20 (R=4-tert-butylphenyl)
Exemplified Compound 21 (R=2-methylphenyl)
Exemplified Compound 24 (R=8-quinolyl)

2-1. Synthesis of Compound 18b

A solution of 60.9 g (0.345 mol) of sodium hydrosulfite in 200 ml of water was added dropwise to a solution of 15.0 g (0.0697 mol) of compound 2a in 150 ml of tetrahydrofuran with stirring at room temperature in an atmosphere of nitrogen. After stirring for 2 hours, 150 ml of ethyl acetate was added, and then, a solution of 12.0 g (0.143 mol) of sodium hydrogencarbonate in 120 ml of water was added dropwise. Further, a solution of 5.2 g (0.0196 mol) of trimesoyl chloride in 50 ml of ethyl acetate was added dropwise, followed by stirring at room temperature for 3 hours. Saturated brine was added to the reaction solution, followed by extraction with ethyl acetate. Then, an organic phase was washed with saturated brine, and dried on anhydrous magnesium sulfate. The solvent was removed by distillation under reduced pressure, and purification was carried out by silica gel column chromatography (developing solvent: chloroform/methanol=10/1(vol./vol.)). Then, recrystallization from dimethylformamide/ acetonitrile was conducted, thereby obtaining 4.1 g (5.76 mmol) of compound 18b. The yield was 29%.

2-2. Synthesis of Exemplified Compound 18

Xylene (100 ml) was added to 3.70 g (5.20 mmol) of compound 18b and 0.7 g (3.68 mmol) of p-toluenesulfonic acid monohydrate, and the resulting solution was refluxed under heating for 3 hours in an atmosphere of nitrogen to conduct azeotropic dehydration. The reaction solution was cooled to room temperature, and then, the solvent was removed by distillation under reduced pressure. After purification by silica gel column chromatography (developing solvent: chloroform/methanol=20/1(vol./vol.)), recrystallization from chloroform/methanol was conducted to obtain 1.70 g (2.58 mmol) of exemplified compound 18. The yield was 50%, and the melting point was from 279° C. to 281° C.

Synthesis Example 3

Synthesis of Exemplified Compound 19a 3-1. Synthesis of Compound 19a m-Toluidine (45.0 g (0.420 mol)) was added to 50.0 g (0.315 mol) of 2-chloro-3-nitropyridine, 90.8 g (0.657 mol) of potassium carbonate, 7.90 g (0.0416 mol) of copper(I) iodide and 300 ml of toluene with stirring at room temperature in an atmosphere of nitrogen. After reflux under heating for 8 hours, the reaction solution was filtered, and the filtrate was concentrated under reduced pressure. After purification by silica gel column chromatography (developing solvent: chloroform), recrystallization from chloroform/hexane was conducted to obtain 51.0 g (0.222 mol) of compound 19a. The yield was 71%.

3-2. Synthesis of Compound 19b

A solution of 124 g (0.712 mol) of sodium hydrosulfite in 320 ml of water was added dropwise to a solution of 32.5 g (0.142 mol) of compound 19a in 320 ml of tetrahydrofuran with stirring at room temperature in an atmosphere of nitrogen. Then, 100 ml of methanol was further added. After stirring for 1 hour, 380 ml of ethyl acetate was added, and then, a solution of 24.4 g (0.290 mol) of sodium hydrogencarbonate in 55 ml of water was added dropwise. Further, a solution of 10.5 g (0.0396 mol) of trimesoyl chloride in 100 ml of ethyl acetate was added dropwise, followed by stirring at room temperature for 3 hours. Saturated brine was added to the reaction solution, followed by extraction with ethyl acetate. Then, an organic phase was washed with saturated brine, and dried on anhydrous magnesium sulfate. The solvent was removed by distillation under reduced pressure, and purification was carried out by silica gel column chromatography (developing solvent: chloroform/methanol=10/1(vol./vol.)), thereby obtaining 10.2 g (0.0135 mol) of compound 19b. The yield was 34%.

3-3. Synthesis of Exemplified Compound 19

Xylene (50 ml) was added to 3.30 g (4.38 mmol) of compound 19b and 0.5 g (2.63 mmol) of p-toluenesulfonic acid monohydrate, and the resulting solution was refluxed under heating for 3 hours in an atmosphere of nitrogen to conduct azeotropic dehydration. The reaction solution was cooled to room temperature, and then, the solvent was removed by distillation under reduced pressure. After purification by silica gel column chromatography (developing solvent: chloroform/methanol=20/1(vol./vol.)), recrystallization from chloroform/methanol was conducted to obtain 1.97 g (2.81 mmol) of exemplified compound 19. The yield was 64%, and the melting point was from 258° C. to 259° C.

Synthesis Example 4

Synthesis of Exemplified Compound 20

4-1. Synthesis of Compound 20a 4-tert-Butylaniline (40.0 g (0.268 mol)) was added to 45.5 g (0.286 mol) of 2-chloro-3-nitropyridine, 81.1 g (0.587 mol) of potassium carbonate, 7.10 g (0.0373 mol) of copper (I) iodide and 300 ml of toluene with stirring at room temperature in an atmosphere of nitrogen. After reflux under heating for 8 hours, the reaction solution was filtered, and the filtrate was concentrated under reduced pressure. After purification by silica gel column chromatography (developing solvent: chloroform), recrystallization from chloroform/hexane was conducted to obtain 52.0 g (0.192 mol) of compound 20a. The yield was 72%.

4-2. Synthesis of Compound 20b

A solution of 112 g (0.643 mol) of sodium hydrosulfite in 320 ml of water was added dropwise to a solution of 34.8 g (0.128 mol) of compound 20a in 350 ml of tetrahydrofuran with stirring at room temperature in an atmosphere of nitrogen, and subsequently, 90 ml of methanol was added. After stirring for 1 hour, 350 ml of ethyl acetate was added, and then, a solution of 22.0 g (0.262 mol) of sodium hydrogencarbonate in 50 ml of water was added dropwise. Further, a solution of 9.5 g (0.0358 mol) of trimesoyl chloride in 90 ml of ethyl acetate was added dropwise, followed by stirring at room temperature for 2 hours. Saturated brine was added to the reactionsolution, followed by extraction with ethyl acetate. Then, an organic phase was washed with saturated brine, and dried on anhydrous magnesium sulfate. The solvent was removed by distillation under reduced pressure, and purification was carried out by silica gel column chromatography (developing solvent: chloroform/methanol=10/1(vol./vol.)), thereby obtaining 12.0 g (0.0136 mol) of compound 20b. The yield was 38%.

4-3. Synthesis of Exemplified Compound 20

Xylene (50 ml) was added to 3.00 g (3.41 mmol) of compound 20b and 0.3 g (1.58 mmol) of p-toluenesulfonic acid monohydrate, and the resulting solution was refluxed under heating for 3 hours in an atmosphere of nitrogen to conduct azeotropic dehydration. The reaction solution was cooled to room temperature. Then, a solid precipitated was taken by filtration, and recrystallized from chloroform/ methanol, thereby obtaining 2.06 g (2.49 mmol) of exemplified compound 20. The yield was 73%, and the melting point was 300° C. or more.

Synthesis Example 5

Synthesis of Exemplified Compound 21

5-1. Synthesis of Compound 21a o-Toluidine (45.0 g (0.420 mol)) was added to 50.0 g (0.315 mol) of 2-chloro-3-nitropyridine, 90.8 g (0.657 mol) of potassium carbonate, 7.90 g (0.0416 mol) of copper(I) iodide and 300 ml of toluene with stirring at room temperature in an atmosphere of nitrogen. After reflux under heating for 8 hours, the reaction solution was filtered, and the filtrate was concentrated under reduced pressure. After purification by silica gel column chromatography (developing solvent: chloroform), recrystallization from chloroform/hexane was conducted to obtain 46.3 g (0.202 mol) of compound 21a. The yield was 64%.

5-2. Synthesis of Compound 21b

A solution of 124 g (0.712 mol) of sodium hydrosulfite in 320 ml of water was added dropwise to a solution of 32.5 g (0.142 mol) of compound 21a in 320 ml of tetrahydrofuran with stirring at room temperature in an atmosphere of nitrogen. Then, 100 ml of methanol was further added. After stirring for 1 hour, 380 ml of ethyl acetate was added, and then, a solution of 24.4 g (0.290 mol) of sodium hydrogencarbonate in 55 ml of water was added dropwise. Further, a solution of 10.5 g (0.0396 mol) of trimesoyl chloride in 100 ml of ethyl acetate was added dropwise, followed by stirring at room temperature for 3 hours. Saturated brine was added to the reaction solution, followed by extraction with ethyl acetate. Then, an organic phase was washed with saturated brine, and dried on anhydrous magnesium sulfate. The solvent was removed by distillation under reduced pressure, and purification was carried out by silica gel column chromatography (developing solvent: chloroform/methanol=10/1(vol./vol.)), thereby obtaining 8.5 g (0.0112 mol) of compound 21b. The yield was 28%.

5-3. Synthesis of Exemplified Compound 21

Xylene (50 ml) was added to 3.30 g (4.38 mmol) of compound 21b and 0.5 g (2.63 mmol) of p-toluenesulfonic acid monohydrate, and the resulting solution was refluxed under heating for 7 hours in an atmosphere of nitrogen to conduct azeotropic dehydration. The reaction solution was cooled to room temperature, and then, the solvent was removed by distillation under reduced pressure. After purification by silica gel column chromatography (developing solvent: chloroform/methanol=20/1(vol./vol.)), recrystallization from chloroform/acetonitrile was conducted to obtain 2.02 g (2.88 mmol) of exemplified compound 21. The yield was 66%, and the melting point was 250° C.

Synthesis Example 6

Synthesis of Exemplified Compound 24

6-1. Synthesis of Compound 24a

8-Aminoquinoline (75.0 g (0.520 mol)) was added to 59.0 g (0.347 mol) of 2-chloro-3-nitropyridine, 105 g (0.760 mol) of potassium carbonate, 9.40 g (0.0494 mol) of copper(I) iodide and 300 ml of toluene with stirring at room temperature in an atmosphere of nitrogen. After reflux under heating for 16 hours, the reaction solution was filtered, and the filtrate was concentrated under reduced pressure. After purification by silica gel column chromatography (developing solvent: chloroform), recrystallization from chloroform/hexane was conducted to obtain 27.0 g (0.102 mol) of compound 24a. The yield was 29%.

6-2. Synthesis of Compound 24b

A solution of 82.2 g (0.472 mol) of sodium hydrosulfite in 420 ml of water was added dropwise to a solution of 25.0 g (93.9 mmol) of compound 24a in 220 ml of tetrahydrofuran with stirring at room temperature in an atmosphere of nitrogen, followed by addition of 70 ml of methanol. After stirring for 1 hour, 380 ml of ethyl acetate was added, and then, a solution of 24.4 g (0.290 mol) of sodium hydrogencarbonate in 55 ml of water was added dropwise. Further, a solution of 7.55 g (28.4 mmol) of trimesoyl chloride in 100 ml of ethyl acetate was added dropwise, followed by stirring at room temperature for 3 hours. Saturated brine was added to the reactionsolution, followed by extraction with ethyl acetate. Then, an organic phase was washed with saturated brine, and dried on anhydrous magnesium sulfate. The solvent was removed by distillation under reduced pressure, and purification was carried out by silica gel column chromatography (developing solvent: chloroform/methanol=10/1(vol./vol.)), thereby obtaining 7.86 g (9.09 mmol) of compound 24b. The yield was 32%.

6-3. Synthesis of Exemplified Compound 24

Xylene (100 ml) was added to 5.00 g (5.78 mmol) of compound 24b and 0.5 g (2.63 mmol) of p-toluenesulfonic acid monohydrate, and the resulting solution was refluxed under heating for 5 hours in an atmosphere of nitrogen to conduct azeotropic dehydration. The reaction solution was cooled to room temperature, and then, the solvent was removed by distillation under reduced pressure. After purification by silica gel column chromatography (developing solvent: chloroform/methanol=20/1(vol./vol.)), recrystallization from chloroform/acetonitrile was conducted to obtain 1.87 g (2.31 mmol) of exemplified compound 24. The yield was 40%, and the melting point was 384° C.

Synthesis Example 7

Synthesis of Exemplified Compound 101

7-1. Synthesis of Compound 101b

A solution of 200 g (1.149 mol) of sodium hydrosulfite in 700 ml of water was added dropwise to a solution of 50.0 g (0.232 mol) of compound 2a in 500 ml of tetrahydrofuran with stirring at room temperature in an atmosphere of nitrogen. Then, 20 ml of methanol was further added. After stirring for 1 hour, 500 ml of ethyl acetate was added, and then, a solution of 40 g (0.476 mol) of sodium hydrogencarbonate in 400 ml of water was added dropwise. Further, a solution of 65.4 g (0.232 mol) of 5-bromoisophthaloylchloride in 150 ml of ethyl acetate was added dropwise, followed by stirring at room temperature for 5 hours. Saturated brine was added to the reaction solution, followed by extraction withethyl acetate. Then, an organic phase was washed with water, saturated brine, and dried on anhydrous magnesium sulfate. The solvent was removed by distillation under reduced pressure, purification was carried out by silica gel column chromatography (developing solvent: chloroform), and recrystallization from chloroform/hexane was conducted to obtain 29.6 g (0.051 mol) of compound 101b. The yield was 22%.

7-2. Synthesis of Compound 101c

Xylene (1 liter) was added to 30 g (0.05 mol) of compound 101b and 4.7 g (0.025 mol) of p-toluenesulfonic acid monohydrate, and the resulting solution was refluxed under heating for 2 hours in an atmosphere of nitrogen to conduct azeotropic dehydration. The reaction solution was cooled to room temperature, and then, the solvent was removed by distillation under reduced pressure. Then, recrystallization from chloroform/ethanol was conducted to obtain 16.3 g (0.03 mol) of exemplified compound 101c. The yield was 58%.

7-3. Synthesis of Exemplified Compound 101

Compound 101c (500 mg (0.92 mmol)) and compound 101d (332 mg (1.01 mmol) were suspended in a solution of 20 ml of ethylene glycol dimethylether and 10 ml of water. To the thus obtained suspension, 214.5 mg (2.02 mmol) of sodium carbonate, 15 mg of palladium carbon and 12 mg of triphenylphosphine were added, and the solution was refluxed under heating for 2 hours. After the termination of heating, the reaction solution was filtered under heating to remove the catalyst. After the filtrate was extracted with ethyl acetate, it was dried on anhydrous magnesium sulfate and the solvent was removed by distillation. The residue was recrystallized from chloroform to obtain 180 mg (0.27 mmol) of exemplified compound 101. The yield was 29%.

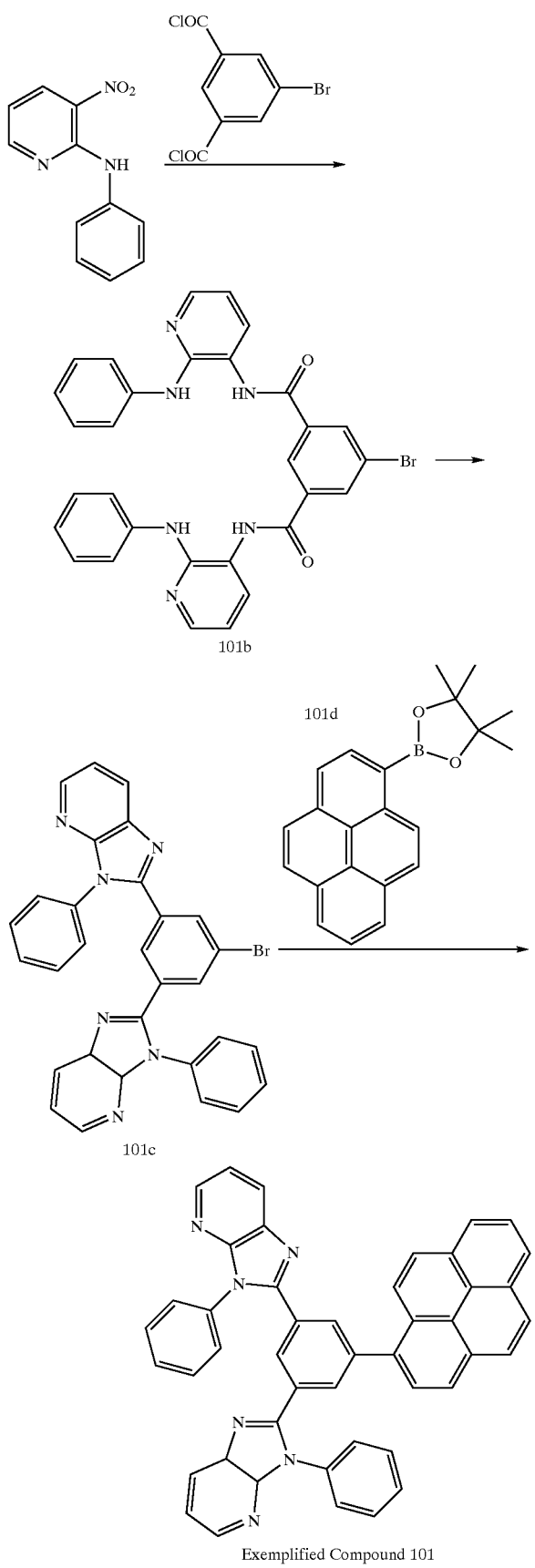

Exemplified Compound 101

The light emitting devices containing the compounds of the invention are described below. Although there is no particular limitation on methods for forming organic layers of the light emitting devices containing the compounds of the invention, methods such as resistance heating vapor deposition, electron beam processing, sputtering, molecular lamination, coating, inkjet process and printing are used. In terms of their characteristics and production, resistance heating vapor deposition and coating are preferred.

When the compounds of the invention are used as the materials for the light emitting devices, they may be used as any of hole injection-transporting layers, electron injection-transporting layers and light emitting layers. However, they are preferably used as electron injection-transporting layers and/or light emitting layers.

The light emitting device of the invention is an element in which a light emitting layer or a plurality of organic compound films including a light emitting layer are formed between a pair of electrodes, an anode and a cathode, and may have a hole injection layer, a hole transporting layer, an electron injection layer, an electron transporting layer and/or a protective layer, in addition to the light emitting layer. Each of these layers may be provided with another function. Various materials can be used for the formation of the respective layers.

The anodes supply holes to the hole injection layers, the hole transporting layers and the light emitting layers, and can be formed of metals, alloys, metal oxides, electric conductive compounds or mixtures thereof, preferably materials having a work function of 4 eV or more. Specific examples thereof include conductive metal oxides such as tin oxide, zinc oxide, indium oxide and indium tin oxide (ITO), metals such as gold, silver, chromium and nickel, further mixtures or laminates of the metals with the conductive metal oxides, inorganic conductive materials such as copper iodide and copper sulfide, organic conductive materials such as polyaniline, polythiophene and polypyrrole, and laminates thereof with ITO. Preferred are conductive metal oxides, and ITO is particularly preferred in terms of productivity, high conductivity and transparency. The thickness of the anode is usually preferably from 10 nm to 5 μm, more preferably from 50 nm to 1 μm, and still more preferably from 100 nm to 500 nm, although it can be appropriately selected depending on the kind of material.

As the anode, one in which layer formation is carried out on soda-lime glass, non-alkali glass or a transparent resin substrate is usually used. When glass is used, non-alkali glass is preferably used for decreasing ions eluted from glass. When soda lime-glass is used, it is preferable to use one provided with a barrier coat of silica or the like. There is no particular limitation on the thickness of the substrate, as long as it is sufficient to keep its mechanical strength. When glass is used, the thickness is usually 0.2 mm or more, and preferably 0.7 mm or more.

Various methods are used for the preparation of the anodes depending on the kind of material. For example, in the case of ITO, film formation is carried out by methods such as electron beam processing, sputtering, resistance heating vapor deposition, chemical reaction (sol-gel processing) and coating of a dispersion of ITO.

The anodes are also capable of decreasing the driving voltage of the elements and increasing the light emitting efficiency by washing or other treatment. For example, in the case of ITO, UV-ozone treatment or plazma treatment is effective.

The cathodes supply electrons to the electron injection layers, the electron transporting layers and the light emitting layers, and are selected considering adhesion to layers adjacent to the negative electrodes, such as the electron injection layers, the electron transporting layers and the light emitting layers, ionization potential and stability. As materials for the cathodes, metals, alloys, metal oxides, electric conductive compounds or mixtures thereof can be used. Specific examples thereof include alkali metals (for example, Li, Na, K and Cs) or fluorides and oxides thereof, alkali earth metals (for example, Mg and Ca) or fluorides and oxides thereof, gold, silver, lead, aluminum, sodium-potassium alloys or mixed metals thereof, lithium-aluminum alloys or mixed metals thereof, magnesium-silver alloys or mixed metals thereof, and rare earth metals such as indium and ytterbium. Preferred are materials having a work function of 4 eV or less, and more preferred are aluminum, lithium-aluminum alloys or mixed metals thereof and magnesium-silver alloys or mixed metals thereof. The thickness of the cathode is usually preferably from 10 nm to 5 $\mu$m, more preferably from 50 nm to 1 $\mu$m, and still more preferably from 100 nm to 1 $\mu$m, although it can be appropriately selected depending on the kind of material.

For the preparation of the cathodes, methods such as electron beam processing, sputtering, resistance heating vapor deposition and coating are used. The metals can be vapor deposited as simple substances, or two or more components can be vapor deposited at the same time. Further, it is also possible to vapor deposit the plurality of metals at the same time to form an alloy electrode, or an alloy previously prepared may also vapor deposited.

It is preferred that the sheet resistance of the anodes and the cathodes is so low as several hundred $\Omega$/square or less.

Materials for the light emitting layers may be any, as long as they can form layers having the function of being able to inject holes from the anodes, the hole injection layers or the hole transporting layers and electrons from the cathodes, the electron injection layers or the electron transporting layers, upon electric field application, the function of transporting injected charges, or the function of providing the field of recombination of holes with electrons to emit light. Examples of the compounds used in the light emitting layers include any compounds which emit light from excitation singlet state or emit light from excitation triplet state, and specifically include benzoxazole derivatives, benzimidazole derivatives, benzthiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perynone derivatives, oxadiazole derivatives, aldazine derivatives, pyrazine derivatives, cyclopentadiene derivatives, bis(styryl)anthracene derivatives, quinacridone derivatives, pyrrolopyridine derivatives, thiadiazolopyridine derivatives, cyclopentadiene derivatives, styrylamine derivatives, aromatic dimethylidyne compounds, various metal complexes represented by metal complexes of 8-quinolinol derivatives, transition metal complexes (e.g., orthometal complexes such as tris(2-phenylpyridine)iridium (III)) and rare earth complexes, and polymers such as polythiophene, polyphenylene, polyphenylenevinylene and polyfluorene, as well as the compounds of the invention. Although there is no particular limitation on the thickness of the light emitting layer, it is usually preferably from 1 nm to 5 $\mu$m, more preferably from 5 nm to 1 $\mu$m, and still more preferably from 10 nm to 500 nm.

Although there is no particular limitation on methods for forming the light emitting layers, methods such as resistance heating vapor deposition, electron beam processing, sputtering, molecular lamination, coating (spin coating, casting and dip coating), inkjet process, printing and LB processing are used. Preferred are resistance heating vapor deposition and coating.

Materials for the hole injection layers and the hole transporting layers may be any, as long as they have any of the function of injecting holes from the anodes, the function of transporting holes and the function of blocking electrons injected from the cathodes. Specific examples thereof include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne compounds, polyphiline compounds, polysilane compounds, poly (N-vinylcarbazole) derivatives, aniline copolymers, conductive high molecular oligomers such as thiophene oligomers and polythiophene, and carbon film. Although there is no particular limitation of the thickness of the hole injection layer and the hole transporting layer, it is usually preferably from 1 nm to 5 $\mu$m, more preferably from 5 nm to 1 $\mu$m, and still more preferably from 10 nm to 500 nm. The hole injection layer and the hole transporting layer may have either a monolayer structure comprising one kind or two or more kinds of the above-mentioned materials, or a multi-layer structure having a plurality of layers each comprising the same composition or different compositions.

As methods for forming the hole injection layers and the hole transporting layers, vacuum deposition, LB processing, coating (spin coating, casting and dip coating) of the above-mentioned materials for the hole injection layers and the hole transporting layers dissolved or dispersed in solvents, inkjet process and printing are used. In the case of coating, the materials can be dissolved or dispersed together with resin components. The resin components include, for example, polyvinyl chloride, polycarbonates, polystyrene, polymethyl methacrylate, polybutyl methacrylate, polyesters, polysulfones, polyphenylene, polyphenylene oxide, polybutadiene, poly(N-vinylcarbazole), hydrocarbon resins, ketone resins, phenoxy resins, polyamides, ethyl cellulose, vinyl acetate, ABS resins, polyurethane, melamine resins, unsaturated polyester resins, alkyd resins, epoxy resins and silicone resins.

Materials for the electron injection layers and the electron transporting layers may be any, as long as they have any of the function of injecting electrons from the cathodes, the function of transporting electrons and the function of blocking holes injected from the anodes. Preferred are the electron injection layers and/or the electron transporting layers containing the compounds of the invention. However, materials other than the compounds of the invention can also be used. specific examples thereof include triazole derivatives, oxazole derivatives, oxadiazole derivatives, fluorenone derivatives, anthraquinodimethane derivatives, anthrone derivatives, diphenylquinone derivatives, thiopyran dioxide derivatives, carbodiimide derivatives, fluorenylidenemethane derivatives, distyrylpyrazine derivatives, heterocyclic tetracarboxylic anhydrides such as naphthaleneperylene, phthalocyanine derivatives, and various metal complexes represented by metal complexes of 8-quinolinol derivatives, metallophthalocyanine, and metal complexes each having benzoxazole or benzothiazole as a ligand. Although there is no particular limitation of the thickness of the electron injection layer and the electron transporting layer, it is usually preferably from 1 nm to 5 μm, more preferably from 5 nm to 1 μm, and still more preferably from 10 nm to 500 nm. The electron injection layer and the electron transporting layer may have either a monolayer structure comprising one kind or two or more kinds of the above-mentioned materials, or a multilayer structure having a plurality of layers each comprising the same composition or different compositions.

As methods for forming the electron injection layers and the electron transporting layers, vacuum deposition, LB processing, coating (spin coating, casting and dip coating) of the above-mentioned materials for the hole injection layers and the hole transporting layers dissolved or dispersed in solvents, inkjet process and printing are used. In the case of coating, the materials can be dissolved or dispersed together with resin components. As the resin components, for example, ones illustrated in the case of the hole injection layers and the hole transporting layers can be applied.

Materials for the protective layers may be any, as long as they have the function of inhibiting promoters of element deterioration such as water and oxygen from entering the elements. Specific examples thereof include metals such as In, Sn, Pb, Au, Cu, Ag, Al, Ti and Ni, metal oxides such as MgO, SiO, $SiO_2$, $Al_2O_3$, GeO, NiO, CaO, BaO, $Fe_2O_3$, $Y_2O_3$ and $TiO_2$, metal fluorides such as $MgF_2$, LiF, $AlF_3$ and $CaF_2$, polyethylene, polypropylene, polymethyl methacrylate, polyimides, polyureas, polytetrafluoroethylene, polychlorotrifluoroethylene, polydichlorodifluoroethylene, copolymers of chlorotrifluoroethylene and dichlorodifluoroethylene, copolymers obtained by copolymerizing monomer mixtures each containing tetrafluoroethylene and at least one kind of comonomer, fluorine-containing copolymers having cyclic structures on main chains of the copolymers, water-absorptive substances having a water absorption of 1% or more, and moisture-proof substances having a water absorption of 0.1% or less.

There is no particular limitation on methods for forming the protective layers. For example, vacuum deposition, sputtering, reactive sputtering, MBE (molecular beam epitaxy), cluster ion beam processing, ion plating, plasma polymerization (high-frequency excitation ion plating), plasma CVD, laser CVD, thermal CVD, gas source CVD, coating, inkjet process and printing can be applied.

The invention will be further illustrated in detail below with reference to the following examples, which are, however, not to be construed as limiting the invention.

EXAMPLE 1

On a washed glass substrate provided with an ITO electrode, a copper phthalocyanine layer having a thickness of 15 nm, an N,N'-bis(1-naphthyl)-N,N'-diphenylbenzidine (NPD) layer having a thickness of 40 nm, and a layer of a compound shown in Table 1, having a thickness of 60 nm were formed in this order by vacuum deposition ($1.0\times10^{-3}$ to $1.3\times10^{-3}$ Pa). A mask patterned (a mask giving a light emitting area of 4 mm×5 mm) was placed thereon, and magnesium/silver of 10/1 were concurrently vapor deposited to a thickness of 250 nm, followed by vapor deposition of silver to a thickness of 300 nm ($1.0\times10^{-3}$ to $1.3\times10^{-3}$ Pa). Thus, a light emitting device was prepared. The device prepared was sealed in a dried glove box.

With a 2400 type source measure unit manufactured by Toyo Technica Corp., a direct current constant voltage was applied to the light emitting device to allow the element to emit light, using ITO as an anode and Mg/Ag as a cathode. The luminance was measured with a BM-8 luminance meter manufactured by Topcon Corp., and the light emitting wavelength and the chromaticity coordinates (CIE chromaticity coordinates) were measured with a PMA-11 spectrum analyzer manufactured by Hamamatsu Photonics K. K. The element prepared was allowed to stand under the conditions of 85° C. and 70% RH for 3 days, and then, allowed to emit light. A relative luminance at that time (a value representing a luminance after aging by a relative value, taking a luminance just after the preparation of the element as 100 (driving voltage: 10V)) and the presence or absence of dark spots (portions at which light is not emitted) were visually observed. Results thereof are shown in Table 1.

TABLE 1

| Sample No. | Compound | Light Emitting Wavelength λmax (nm) | Maximum Luminance (cd/m$^2$) | CIE Chromaticity Coordinates (X, Y) |
|---|---|---|---|---|
| 101 | Comparative Compound 1 | 460 | 410 | (0.16, 0.15) |
| 102 | Comparative Compound 2 | 445 | 230 | (0.15, 0.15) |
| 103 | Exemplified Compound 2 | 465 | 1620 | (0.16, 0.15) |
| 104 | Exemplified Compound 18 | 463 | 1777 | (0.16, 0.16) |
| 105 | Exemplified Compound 19 | 447 | 1650 | (0.16, 0.17) |
| 106 | Exemplified Compound 21 | 420 | 1820 | (0.15, 0.13) |
| 107 | Exemplified Compound 24 | 432 | 1900 | (0.15, 0.14) |

| Sample No. | Minimum Driving Voltage (V) | Relative Luminance after Aging | Occurrence Of Dark Spots | Note |
|---|---|---|---|---|
| 101 | 6 | 77 | No | Comparison |
| 102 | 7 | 12 | Yes | Comparison |
| 103 | 4 | 82 | No | Invention |
| 104 | 4 | 91 | No | Invention |
| 105 | 4 | 88 | No | Invention |
| 106 | 4 | 93 | No | Invention |
| 107 | 4 | 94 | No | Invention |

Comparative Compound 1

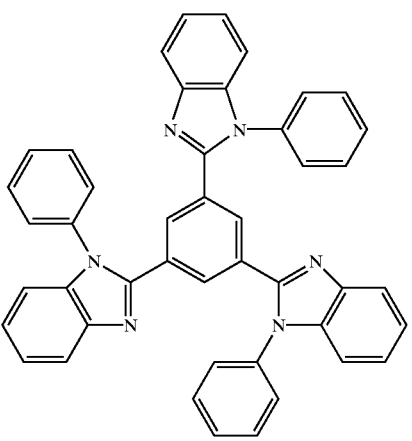

Compound described in JP-A-10-92578

Comparative Compound 2 (PBD)

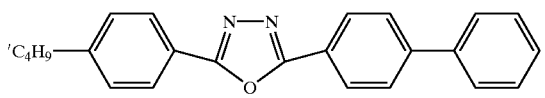

The results of Table 1 show that the use of the compounds of the invention makes it possible to emit blue light of high luminance and good color purity, even in the case of non-doped elements, and also indicate that a decrease in luminance and the occurrence of dark spots after storage at high temperatures are slight, resulting in excellent durability.

EXAMPLE 2

After an ITO substrate was washed in the same manner as with Example 1, a copper phthalocyanine layer having a thickness of 5 nm, an NPD layer having a thickness of 40 nm, a blue light emitting material A layer having a thickness of 20 nm and a layer of a compound shown in Table 2, having a thickness of 40 nm were formed in this order by vacuum deposition ($1.0 \times 10^{-3}$ to $1.3 \times 10^{-3}$ Pa). A mask pattened (a mask giving a light emitting area of 4 mm×5 mm) was placed thereon, and magnesium/silver of 10/1 were concurrently vapor deposited to a thickness of 250 nm, Blue Light Emitting Material A

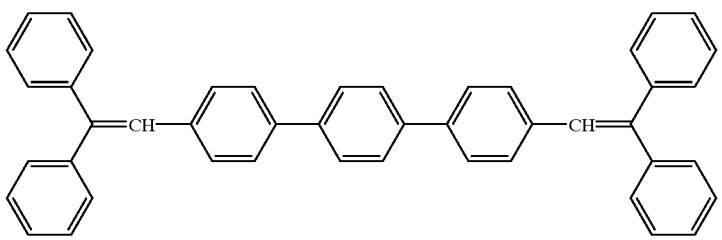

followed by vapor deposition of silver to a thickness of 300 nm ($1.0 \times 10^{-3}$ to $1.3 \times 10^{-3}$ Pa). Thus, a light emitting device was prepared. The device prepared was sealed in a dried glove box.

The elements prepared were evaluated in the same manner as with example 1. Results thereof are shown in Table 2.

TABLE 2

| Sample No. | Compound | Light Emitting Wavelength λmax (nm) | Maximum Luminance (cd/m²) | CIE Chromaticity Coordinates (X, Y) |
|---|---|---|---|---|
| 201 | Comparative Compound 1 | 460 | 510 | (0.15, 0.15) |
| 202 | Comparative Compound 2 | 462 | 320 | (0.15, 0.15) |
| 203 | Exemplified Compound 18 | 462 | 3040 | (0.15, 0.15) |
| 204 | Exemplified Compound 19 | 462 | 2780 | (0.15, 0.16) |
| 205 | Exemplified Compound 21 | 461 | 3820 | (0.15, 0.14) |
| 206 | Exemplified Compound 24 | 462 | 4040 | (0.15, 0.14) |
| 207 | Exemplified Compound 26 | 461 | 2650 | (0.15, 0.15) |
| 208 | Exemplified Compound 81 | 464 | 2430 | (0.15, 0.15) |

TABLE 2-continued

| Sample No. | Minimum Driving Voltage (V) | Relative Luminance after Aging | Occurrence Of Dark Spots | Note |
|---|---|---|---|---|
| 201 | 6 | 79 | No | Comparison |
| 202 | 7 | 19 | Yes | Comparison |
| 203 | 4 | 83 | No | Invention |
| 204 | 4 | 82 | No | Invention |
| 205 | 4 | 94 | No | Invention |
| 206 | 4 | 98 | No | Invention |
| 207 | 4 | 81 | No | Invention |
| 208 | 4 | 80 | No | Invention |

Comparative Compounds 1 and 2 were the same as with Example 1.

The results of Table 2 show that when the compounds of the invention are used, they function as electron transporting materials in non-doped elements to make it possible to emit blue light of high luminance and good color purity, and also indicate that a decrease in luminance and the occurrence of dark spots after storage at high temperatures are slight, resulting in excellent durability.

EXAMPLE 3

After an ITO substrate was washed in the same manner as with Example 1, a copper phthalocyanine layer having a thickness of 5 nm, an NPD layer having a thickness of 40 nm, and a layer of perylene and a compound shown in Table 3 were formed by vapor deposition. Perylene and a compound shown in Table 3 were concurrently vapor deposited so as to give a thickness of 60 nm at vapor deposition rates of 0.04 nm/second and 0.4 nm/second, respectively ($1.0 \times 10^{-3}$ to $1.3 \times 10^{-3}$ Pa). A mask patterned (a mask giving a light emitting area of 4 mm×5 mm) was placed thereon, and magnesium/silver of 10/1 were concurrently vapor deposited to a thickness of 250 nm, followed by vapor deposition of silver to a thickness of 300 nm ($1.0 \times 10^{-3}$ to $1.3 \times 10^{-3}$ Pa). Thus, alight emitting device was prepared. The device prepared was sealed in a dried glove box.

For the elements prepared, the luminance and the chromaticity at driving voltages of 8 V and 15 V were measured (the luminance was measured with a BM-8 luminance meter manufactured by Topcon Corp., and the chromaticity was measured with a PMA-11 spectrum analyzer manufactured by Hamamatsu Photonics K. K.). Results thereof are shown in Table 3.

which allows luminescence of high luminance high in color purity.

EXAMPLE 4

Poly(N-vinylcarbazole) (40 mg), 10.0 mg of blue light emitting material B, 2.0 mg of green light emitting material G, 0.5 mg of red light emitting material R and 12.0 g of a compound described in Table 4 were dissolved in 3 ml of 1,2-dichloroethane, and the resulting solution was applied

TABLE 3

| Sample No. | Compound | Maximum Luminance (cd/m²) Driven at 8 V | Maximum Luminance (cd/m²) Driven at 15 V | CIE Chromaticity Coordinates (x, y) Driven at 8 V | CIE Chromaticity Coordinates (x, y) Driven at 15 V | Note |
|---|---|---|---|---|---|---|
| 301 | Comparative Compound 3 | 475 | 2250 | (0.15, 0.15) | (0.17, 0.25) | Comparison |
| 302 | Exemplified Compound 5 | 920 | 2890 | (0.15, 0.15) | (0.15, 0.16) | Invention |
| 303 | Exemplified Compound 18 | 1040 | 3130 | (0.15, 0.15) | (0.15, 0.16) | Invention |
| 304 | Exemplified Compound 27 | 860 | 2840 | (0.15, 0.15) | (0.15, 0.15) | Invention |
| 305 | Exemplified Compound 82 | 740 | 2600 | (0.15, 0.15) | (0.15, 0.16) | Invention |

Comparative Compound 3 (Alq)

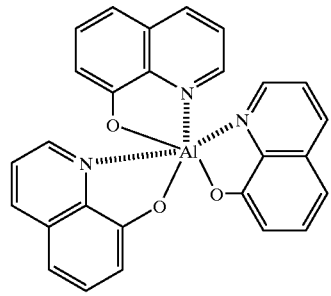

As apparent from the results of Table 3, according to the elements using the compounds of the invention, luminescence of high luminance is possible even in the system doped with the fluorescent compound. Further, the results show that in the element using Alq as a host, an increase in driving voltage results in a decrease in blue color purity, whereas in the elements using the compounds of the invention as hosts, changes in color purity are scarcely observed, onto a washed ITO substrate by spin coating. The thickness of an organic film formed was about 110 nm. A mask patterned (a mask giving a light emitting area of 4 mm×5 mm) was placed thereon, and then Al/Li of 100/2 were concurrently vapor deposited to a thickness of 200 nm to prepare a light emitting device.

The devices prepared were evaluated in the same manner as with Example 1. Results thereof are shown in Table 4.

TABLE 4

| Sample No. | Compound | Minimum Driving Voltage (V) | Maximum Luminance (cd/m²) | CIE Chromaticity Coordinates (x, y) | Occurrence of Dark Spots | Note |
|---|---|---|---|---|---|---|
| 401 | Comparative Conpound 2 | 14 | 425 | (0.32, 0.35) | Yes | Comparison |
| 402 | Exemplified Compound 3 | 9 | 3030 | (0.34, 0.35) | No | Invention |
| 403 | Exemplified Compound 4 | 9 | 2760 | (0.34, 0.36) | No | Invention |
| 404 | Exemplified Compound 5 | 8 | 3270 | (0.33, 0.36) | No | Invention |

TABLE 4-continued

| Sample No. | Compound | Minimum Driving Voltage (V) | Maximum Luminance (cd/m$^2$) | CIE Chromaticity Coordinates (x, y) | Occurrence of Dark Spots | Note |
|---|---|---|---|---|---|---|
| 405 | Exemplified Compound 18 | 8 | 4150 | (0.33, 0.36) | No | Invention |
| 406 | Exemplified Compound 27 | 9 | 3050 | (0.34, 0.35) | No | Invention |

Comparative compound 2 was the same as with Example 1.

Blue Light Emitting Material B

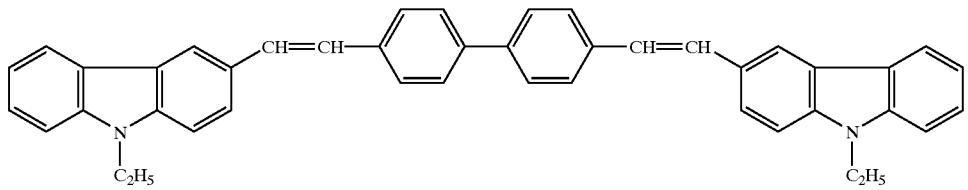

Green Light Emitting Material G

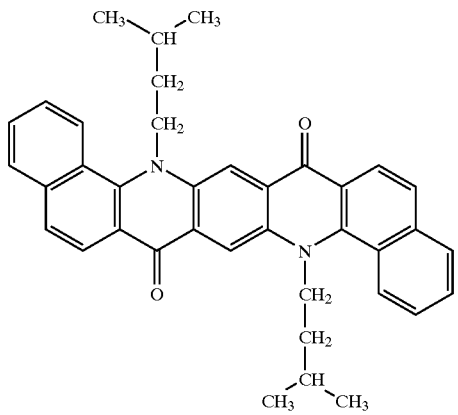

Red Light Emitting Material R

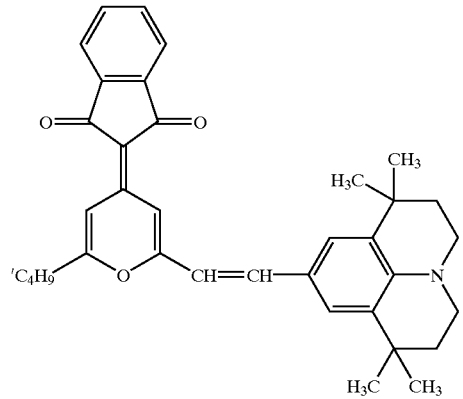

As apparent from the results of Table 4, according to the elements using the compounds of the invention, driving at low voltage and luminescence of high luminance compared with the comparative compound are possible even in the coating system in which the luminance is usually low. Further, in the element using comparative compound 2 (PBD), the occurrence of dark spots is significantly observed, whereas the elements of the invention show good planar luminescence. Furthermore, the results indicate that the combination of the blue, green and red light emitting materials using the compounds of the invention allows good white luminescence.

EXAMPLE 5

After an ITO substrate was washed in the same manner as with Example 1, NPD was vapor deposited to a thickness of 50 nm, and 4,4'-bis(carbazole-9-yl)biphenyl and tris(2-phenylpyridine)iridium (III) were concurrently vapor deposited so as to give a thickness of 20 nm at vapor deposition rates of 0.4 nm/second and 0.025 nm/second, respectively. Then, exemplified compound 21 was vapor deposited to a thickness of 25 nm, and LiF was further vapor deposited ($1.0 \times 10^{-3}$ to $1.3 \times 10^{-3}$ Pa) to a thickness of 1 nm. A mask patterned (a mask giving a light emitting area of 4 mm×5 mm) was placed thereon, and aluminum was vapor deposited to a thickness of 200 nm ($1.0 \times 10^{-3}$ to $1.3 \times 10^{-3}$ Pa), thereby preparing a device. As a result of evaluation of the device thus prepared, green luminescence of high luminance and high efficiency showing a maximum luminance of 98,000 cd/m$^2$ and an external quantum efficiency of 14% was obtained.

EXAMPLE 6

After an ITO substrate was washed in the same manner as with Example 1, a Baytron P (PEDOT)-PSS solution (a polydioxyethylene-polystyrenesulfonic acid dope) (manufactured by Bayer AG) was applied onto the substrate by spin coating at 2,000 rpm for 60 seconds, followed by vacuum drying at 100° C. for 1 hour to prepare a hole transporting layer (having a thickness of about 100 nm). A solution of 20 mg of poly(9,9-dioctylfluorene) in 2 ml of chloroform was applied onto the layer by spin coating (1,000 rpm, 20 seconds) to a thickness of about 70 nm. Exemplified compound 18 was vacuum deposited ($1.0 \times 10^{-3}$ to $1.3 \times 10^{-3}$ Pa) thereon to a thickness of 30 nm. Then, a mask patterned (a mask giving a light emitting area of 4 mm×5 mm) was placed thereon, and a cathode was formed by vapor deposition in the same manner as with Example 1 to prepare a device (a device of the invention). For comparison, a device was prepared in the same manner as described above with the exception that exemplified compound 18 was excluded. EL characteristics were evaluated for both devices. As a result, the maximum luminance and the external quantum efficiency were 93 cd/m² and 0.1% or less, respectively, for the device for comparison, whereas the maximum luminance and the external quantum efficiency were 1680 cd/m² and 1.3%, respectively, for the device of the invention, which revealed that the compound of the invention effectively functioned as an electron transporting material even when a π conjugated polymer was used as a light emitting material.

EXAMPLE 7

After an ITO substrate was washed in the same manner as with Example 1, a Baytron P (PEDOT)-PSS solution (a polydioxyethylene-polystyrenesulfonic acid dope) (manufactured by Bayer AG) was applied onto the substrate by spin coating at 2,000 rpm for 60 seconds, followed by vacuum drying at 100° C. for 2 hour to prepare a hole transporting layer (having a thickness of about 100 nm). A solution of 40 mg of poly(N-vinylcarbozol), 12 mg of PBD and 1 mg of tris (2-phenylpyridine) iridium(III) in 3 ml of chloroform was applied onto the layer by spin coating (1,500 rpm, 20 seconds) to a thickness of about 80 nm. Exemplified compound 21 was vacuum deposited ($1.0 \times 10^{-3}$ to $1.3 \times 10^{-3}$ Pa) thereon to a thickness of 20 nm, and further LiF was deposited ($1.0 \times 10^{-3}$ to $1.3 \times 10^{-3}$ Pa) thereon to a thickness of about 1 nm. Then, a mask patterned (a mask giving a light emitting area of 4 nm×5 mm) was placed thereon, and aluminum was deposited ($1.0 \times 10^{-3}$ to $1.3 \times 10^{-3}$ Pa) thereon to a thickness of 200 nm to prepare a device (a device of the invention). For comparison, a device was prepared in the same manner as described above with the exception that exemplified compound 21 was excluded. EL characteristics were evaluated for both devices. As a result, the device for comparison showed the external quantum efficiency at the light emitting luminance of 1000 cd/m² of 5.2%, whereas the device of the invention showed the external quantum efficiency at the same light emitting luminance of 10.2%, which revealed that the compound of the invention effectively functioned as an electron transporting material even when tris(2-phenylpyridine)iridium(III), which is a compound emitting light from the excitation triplet state, was used as a light emitting material.

According to the compounds of the invention, for both the doped devices and the non-doped devices, the preparation of the blue light emitting devices good in color purity and high in luminance becomes possible, and the devices that can emit light within a wide wavelength region can be provided. Further, good light emitting characteristics are obtained even in the coating system in which the luminance is usually low, so that the devices can be fabricated advantageously in respect to production cost. Furthermore, the organic light emitting devices good in durability and small in chromaticity changes caused by the difference in driving voltage are obtained.

What is claimed is:
1. A material for a light emitting device consisting of a compound represented by the following general formula (VIII):

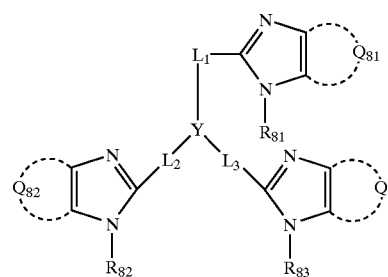

(VIII)

wherein $Q_{81}$, $Q_{82}$ and $Q_{83}$ each represents an atomic group necessary to form a 6-membered nitrogen-containing aromatic heterocycle; $R_{81}$, $R_{82}$ and $R_{83}$ each represents a hydrogen atom, an aliphatic hydrocarbon group, an aryl group or a heterocyclic group; $L_1$, $L_2$ and $L_3$ each represents a connecting group; and Y represents a nitrogen atom or a 1,3,5-benzenetriyl group.

2. A compound represented by the following general formula (IX):

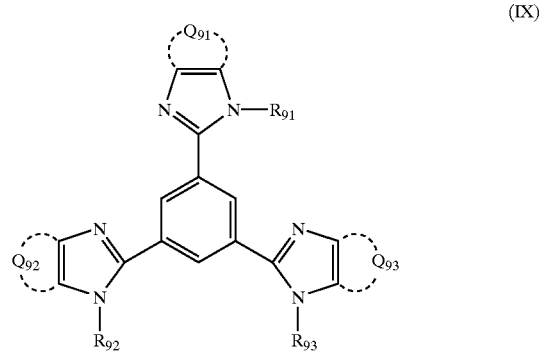

(IX)

wherein $Q_{91}$, $Q_{92}$ and $Q_{93}$ each represents an atomic group necessary to form a 6-membered nitrogen-containing aromatic heterocycle; and $R_{91}$, $R_{92}$ and $R_{93}$ each represents a hydrogen atom, an aliphatic hydrocarbon group, an aryl group or a heterocyclic group.

3. A compound represented by the following general formula (X):

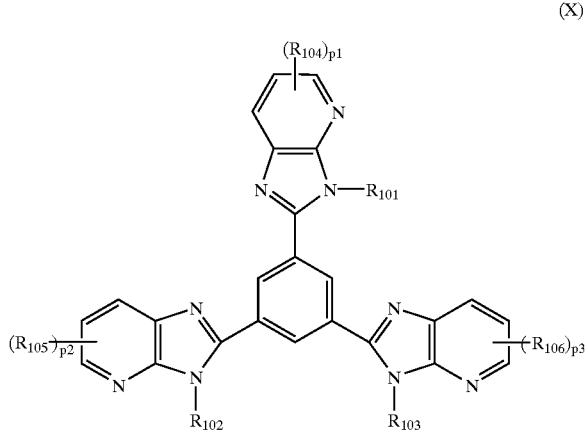

(X)

wherein $R_{101}$, $R_{102}$ and $R_{103}$ each represents a hydrogen atom, an aliphatic hydrocarbon group, an aryl group or a heterocyclic group; $R_{104}$, $R_{105}$ and $R_{106}$ each represents a substituent; and $p_1$, $p_2$ and $p_3$ each represents an integer of 0 to 3.

4. A light emitting device comprising a light emitting layer or a plurality of organic compound films containing a light emitting layer formed between a pair of electrodes, wherein at least one layer is a layer containing at least one of the compounds represented by the following general formula (VIII), (IX) and (X):

(VIII)

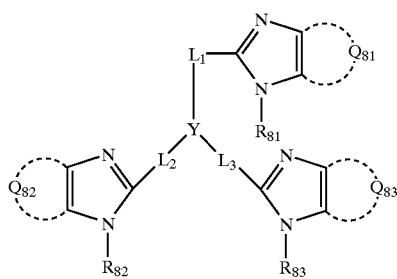

wherein $Q_{81}$, $Q_{82}$ and $Q_{83}$ each represents an atomic group necessary to form a 6-membered nitrogen-containing aromatic heterocycle; $R_{81}$, $R_{82}$ and $R_{83}$ each represents a hydrogen atom, an aliphatic hydrocarbon group, an aryl group or a heterocyclic group; $L_1$, $L_2$ and $L_3$ each represents a connecting group; and Y represents a nitrogen atom or a 1,3,5-benzenetriyl group (IX)

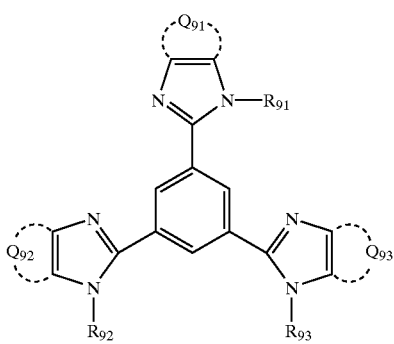

wherein $Q_{91}$, $Q_{92}$ and $Q_{93}$ each represents an atomic group necessary to form a 6-membered nitrogen-containing aromatic heterocycle; and $R_{91}$, $R_{92}$ and $R_{93}$ each represents a hydrogen atom, an aliphatic hydrocarbon group, an aryl group or a heterocyclic group (X)

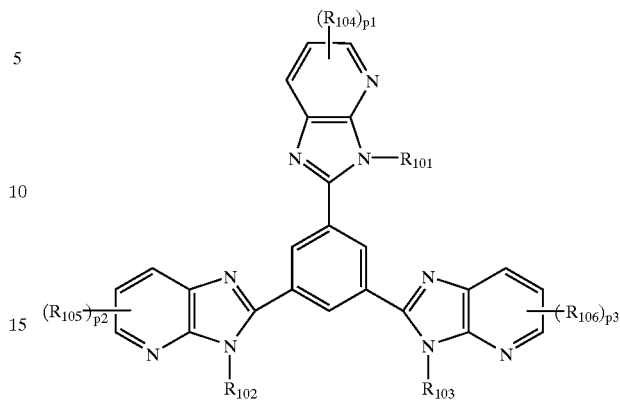

wherein $R_{101}$, $R_{102}$ and $R_{103}$ each represents a hydrogen atom, an aliphatic hydrocarbon group, an aryl group or a heterocyclic group; $R_{104}$, $R_{105}$ and $R_{106}$ each represents a substituent; and $p_1$, $p_2$ and $p_3$ each represents an integer of 0 to 3.

5. A light emitting device comprising a light emitting layer or a plurality of organic compound films containing a light emitting layer formed between a pair of electrodes, wherein at least one layer is a layer in which at least one of the compounds represented by the following general formula (VIII), (IX) and (X) is dispersed in a polymer:

(VIII)

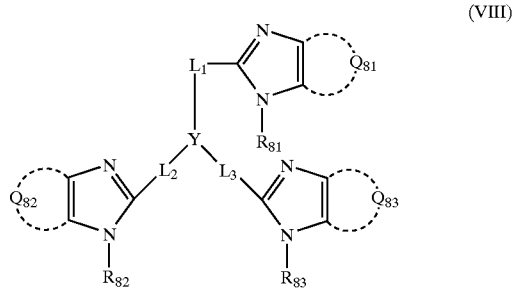

wherein $Q_{81}$, $Q_{82}$ and $Q_{83}$ each represents an atomic group necessary to form a 6-membered nitrogen-containing aromatic heterocycle; $R_{81}$, $R_{82}$ and $R_{83}$ each represents a hydrogen atom, an aliphatic hydrocarbon group, an aryl group or a heterocyclic group; $L_1$, $L_2$ and $L_3$ each represents a connecting group; and Y represents a nitrogen atom or a 1,3,5-benzenetriyl group (IX)

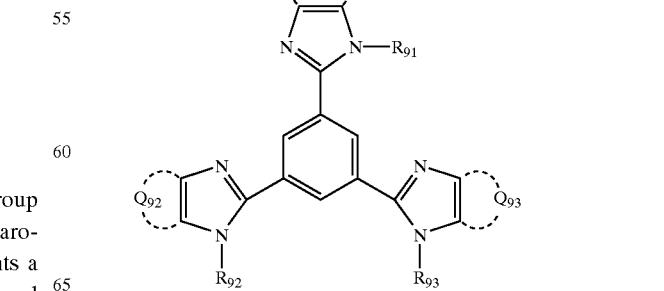

wherein $Q_{91}$, $Q_{92}$ and $Q_{93}$ each represents an atomic group necessary to form a 6-membered nitrogen-containing aromatic heterocycle; and $R_{91}$, $R_{92}$ and $R_{93}$ each represents a hydrogen atom, an aliphatic hydrocarbon group, an aryl group or a heterocyclic group (X)

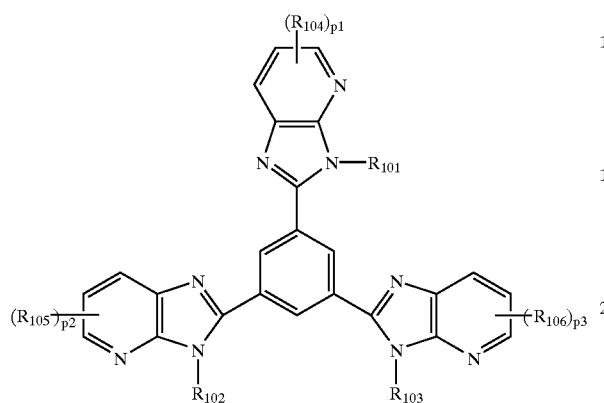

wherein $R_{101}$, $R_{102}$ and $R_{103}$ each represents a hydrogen atom, an aliphatic hydrocarbon group, an aryl group or a heterocyclic group; $R_{104}$, $R_{105}$ and $R_{106}$ each represents a substituent; and $p_1$, $p_2$ and $p_3$ each represents an integer of 0 to 3.

6. A light emitting device comprising a light emitting layer or a plurality of organic compound films containing a light emitting layer formed between a pair of electrodes, wherein at least one layer between the light emitting layer and a cathode is a layer containing at least one of the compounds represented by the following general formula (VIII), (IX) and (X):

(VIII)

wherein $Q_{81}$, $Q_{82}$ and $Q_{83}$ each represents an; atomic group necessary to form a 6-membered nitrogen-containing aromatic heterocycle; $R_{81}$, $R_{82}$ and $R_{83}$ each represents a hydrogen atom, an aliphatic hydrocarbon group, an aryl group or a heterocyclic group; $L_1$, $L_2$ and $L_3$ each represents a connecting group; and Y represents a nitrogen atom or a 1,3,5-benzenetriyl group (IX)

wherein $Q_{91}$, $Q_{92}$ and $Q_{93}$ each represents an atomic group necessary to form a 6-membered nitrogen-containing aromatic heterocycle; and $R_{91}$, $R_{92}$ and $R_{93}$ each represents a hydrogen atom, an aliphatic hydrocarbon group, an aryl group or a heterocyclic group (X)

wherein $R_{101}$, $R_{102}$ and $R_{103}$ each represents a hydrogen atom, an aliphatic hydrocarbon group, an aryl group or a heterocyclic group; $R_{104}$, $R_{105}$ and $R_{106}$ each represents a substituent; and $p_1$, $p_2$ and $p_3$ each represents an integer of 0 to 3.

7. A light emitting device comprising a light emitting layer or a plurality of organic compound films containing a light emitting layer formed between a pair of electrodes, wherein at least one layer between a blue light emitting layer and a cathode is a layer containing at least one of the compounds represented by the following general formula (VIII), (IX) and (X):

(VIII)

wherein $Q_{81}$, $Q_{82}$ and $Q_{83}$ each represents an atomic group necessary to form a 6-membered nitrogen-containing aromatic heterocycle; $R_{81}$, $R_{82}$ and $R_{83}$ each represents a hydrogen atom, an aliphatic hydrocarbon group, an aryl group or a heterocyclic group; $L_1$, $L_2$ and $L_3$ each represents a connecting group; and Y represents a nitrogen atom or a 1,3,5-benzenetriyl group

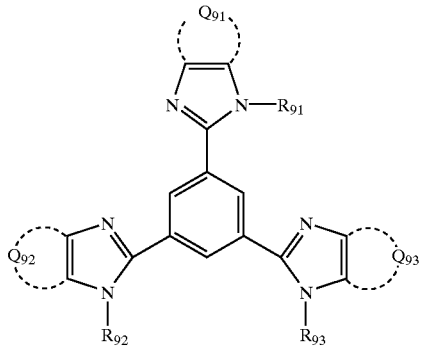

(IX)

wherein $Q_{91}$, $Q_{92}$ and $Q_{93}$ each represents an atomic group necessary to form a 6-membered nitrogen-containing aromatic heterocycle; and $R_{91}$, $R_{92}$ and $R_{93}$ each represents a hydrogen atom, an aliphatic hydrocarbon group, an aryl group or a heterocyclic group

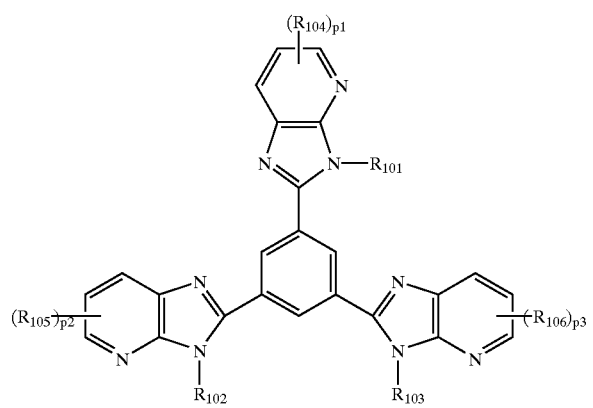

(X)

wherein $R_{101}$, $R_{102}$ and $R_{103}$ each represents a hydrogen atom, an aliphatic hydrocarbon group, an aryl group or a heterocyclic group; $R_{104}$, $R_{105}$ and $R_{106}$ each represents a substituent; and $p_1$, $p_2$ and $p_3$ each represents an integer of 0 to 3.

8. A light emitting device comprising a light emitting layer or a plurality of organic compound films containing a light emitting layer formed between a pair of electrodes, wherein a layer containing at least one of the compounds represented by the following general formula (VIII), (IX) and (X) contains a blue light emitting material:

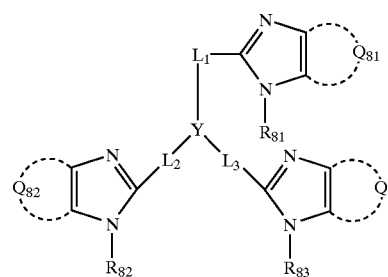

(VIII)

wherein $Q_{81}$, $Q_{82}$ and $Q_{83}$ each represents an atomic group necessary to form a 6-membered nitrogen-containing aromatic heterocycle; $R_{81}$, $R_{82}$ and $R_{83}$ each represents a hydrogen atom, an aliphatic hydrocarbon group, an aryl group or a heterocyclic group; $L_1$, $L_2$ and $L_3$ each represents a connecting group; and Y represents a nitrogen atom or a 1,3,5-benzenetriyl group (IX)

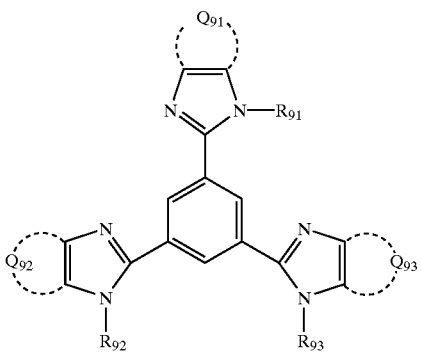

wherein $Q_{91}$, $Q_{92}$ and $Q_{93}$ each represents an atomic group necessary to form a 6-membered nitrogen-containing aromatic heterocycle; and $R_{91}$, $R_{92}$ and $R_{93}$ each represents a hydrogen atom, an aliphatic hydrocarbon group, an aryl group or a heterocyclic group (X)

wherein $R_{101}$, $R_{102}$ and $R_{103}$ each represents a hydrogen atom, an aliphatic hydrocarbon group, an aryl group or a heterocyclic group; $R_{104}$, $R_{105}$ and $R_{106}$ each represents a substituent; and $p_1$, $p_2$ and $p_3$ each represents an integer of 0 to 3.

9. The light emitting device of claim 4, wherein $p_1$, $p_2$ and $p_3$ in the general formula (X) are independently 0 or 1.

10. The light emitting device of claim 4, wherein each of $R_{101}$, $R_{102}$ and $R_{103}$ in the general formula (X) is independently an aryl group.

11. The light emitting device of claim 4, wherein each of $R_{104}$, $R_{105}$ and $R_{106}$ in the general formula (X) is independently an alkyl group.

* * * * *